(12) United States Patent
Murphy

(10) Patent No.: US 6,790,183 B2
(45) Date of Patent: Sep. 14, 2004

(54) METHOD AND APPARATUS FOR DISPLAYING BODY SOUNDS AND PERFORMING DIAGNOSIS BASED ON BODY SOUND ANALYSIS

(76) Inventor: Raymond L. H. Murphy, 38 Cypress Rd., Wellesley, MA (US) 02181

( * ) Notice: Subject to any disclaimer, the term of this patent is extended or adjusted under 35 U.S.C. 154(b) by 43 days.

(21) Appl. No.: 10/080,209

(22) Filed: Feb. 21, 2002

(65) Prior Publication Data

US 2002/0183642 A1 Dec. 5, 2002

Related U.S. Application Data

(63) Continuation-in-part of application No. 09/699,546, filed on Oct. 30, 2000, now Pat. No. 6,394,967, which is a continuation of application No. 09/172,343, filed on Oct. 14, 1998, now Pat. No. 6,139,505.

(51) Int. Cl.[7] ................................................. A61B 5/08
(52) U.S. Cl. ...................................................... 600/532
(58) Field of Search ................................ 600/586, 528, 600/300, 538

(56) References Cited

U.S. PATENT DOCUMENTS

| | | |
|---|---|---|
| 3,990,435 A | 11/1976 | Murphy |
| 4,063,550 A | 12/1977 | Tiep |
| 4,267,845 A | 5/1981 | Robertson, Jr. et al. |
| 4,672,977 A | 6/1987 | Kroll |
| 4,928,705 A | 5/1990 | Sekhar et al. |
| 4,951,678 A | 8/1990 | Joseph et al. |
| 4,991,581 A | 2/1991 | Andries |
| 5,010,889 A | 4/1991 | Bredesen et al. |
| 5,035,247 A | 7/1991 | Heimann |
| 5,165,417 A | 11/1992 | Murphy, Jr. |
| 5,213,108 A | 5/1993 | Bredesen et al. |
| 5,218,969 A | 6/1993 | Bredesen et al. |
| 5,301,679 A | 4/1994 | Taylor |
| 5,329,932 A | 7/1994 | Yount |
| 5,718,227 A | * 2/1998 | Witlin et al. ................. 600/528 |
| 5,825,895 A | 10/1998 | Grasfield et al. |
| 5,844,997 A | 12/1998 | Murphy, Jr. |
| 6,005,951 A | 12/1999 | Grasfield et al. |
| 6,116,241 A | 9/2000 | Huygen et al. |
| 6,139,505 A | 10/2000 | Murphy |
| 6,152,884 A | * 11/2000 | Bjorgaas ...................... 600/528 |
| 6,168,568 B1 | 1/2001 | Gavriely |

OTHER PUBLICATIONS

PCT Notification of Transmittal of the International Search Report or the Declaration, Form PCT/ISA/220 (Apr. 2002).

(List continued on next page.)

*Primary Examiner*—Robert L. Nasser
(74) *Attorney, Agent, or Firm*—Cesari and McKenna, LLP

(57) ABSTRACT

A lung sound diagnostic system for use in collecting, organizing and analyzing lung sounds associated with the inspiration(s) and expiration(s) of a patient. The system includes a plurality of transducers that may be placed at various sites around the patient's chest. The microphones are coupled to signal processing circuitry and A/D converters which digitize the data and preferably provides the digital data to a computer station. A data collection and organization program, executing on the computer station, organizes and formats the data into a combination display for display or printing. The combinational display includes at least two display elements. In a first display element, the data is shown for both inspiration and expiration combined in a first time scale. In a second display element, the data for inspiration and expiration are shown individually in a second time scale that is time-expanded relative to the first time scale. The system may also include application programs for detecting and classifying abnormal sounds. The resulting information may be displayed in a variety of formats to facilitate diagnosis. Additionally, the system may include an analysis program for comparing selected criteria corresponding to the detected abnormal sounds with predefined thresholds in order to provide a likely diagnosis.

11 Claims, 23 Drawing Sheets

OTHER PUBLICATIONS

Earis, J. Woodhouse, N. and Duffy, N., Reproducibility of Crackle Counts in Normals and Patients with Stable Fibrosing Alvelotis, Sep. 2001.

Kompis, M. and Wodicks, G., Spatial Reconstruction of Acoustic Sources in the Thorax, Oct. 1995.

Ishikawa, S., Gomez, F., Vyshedskiy, A., Elmaghhiraby, Z., MacDonnell, K.F. and Cell B., "Expiratory Wheeze" in a Patient with "Vocal Cord Dysfunction", Sep. 2001.

Bergstresser, T., Vyshedskiy, A. and Murphy, R., Sound Speed in the Lung as a Function of Lung Volume, Presented at the annual meeting of the International Lung Sound Association, Berlin, Sep. 2001.

Murphy, R., Vyshedskiy, A., Ramirez, A., Brockington, G., Power, V., Gopal, M., Cohen, J. and Paciej, J., Objective Measurement of Wheezes and Crackles in Congestive Heart Failure and Bronchial Asthma, Presented at the annual meeting of the International Lung Sound Association, Berlin, Sep. 2001.

Murphy, R., Vyshedskiy, A., Power, V-A, Bergstrom, K. and Murphy, M., Objective Measurement of Lung Sounds in Chronic Obstructive Lung Disease, Presented at the annual meeting of the European Respiratory Society, Berlin, Sep. 2001.

Murphy, R., Vyshediskiy, A., Marinelli, P., Bixby, M. Bergstrom, K., V-A Power, Computerized Lung Sounds in Assessment of ICU Patients, Presented at the Annual Meeting of the American Thoracic Society, 2001.

Davidson, F., House, C., Power, V-A, Bergstrom K., Wilson, C. and Vyshedskiy, A., Lung Sound Amplitude and Tidal Volume During Positive Pressure Ventilation, Presented at the annual meeting of the International Lung Sound Association, Berlin, 2001.

Murphy, R., Davidson, F., House, C., Power, V-A, Bergstrom K., Wilson, C. and Vyshedskiy, A., The Relationship of Lung Sound Amplitude and Tidal Volume During Positive Pressure Ventilation, Presented at the annual ACCP meeting, San Franscisco, 2000.

Murphy, R., Bergstrom, K. and Mylott, Characteristics of Lung Sounds in Patients with Pneumonia and Congestive Heart Failure, Presented at the annual meeting of the International Lung Sound Association, 1997.

Ishikawa, S., Murphy, M. and Murphy, M. and Murphy R., "E"–Change in Normal, COPD and Asthmatic Patients, Presented at the $25^{th}$ International Conference on Lung Sounds, Chicago, IL, Sep. 2000.

Bergstresser, T., Vyshedskiy, A. and Murphy, R., Sound Speed in the Lung as a Function of Lung Volume, Presented at the $25^{th}$ International Conference on Lung Sounds, Chicago, IL, Sep. 2000.

Kiyokawa, H. and Pasterkamp, H., Respiratory phase affects the time delay of lung sounds between adjacent sensors, Presented at the $25^{th}$ International Conference on Lung Sounds, Chicago, IL, Sep. 2000.

* cited by examiner

DISCONTINUOUS: CRACKLES

CONTINUOUS: WHEEZE

RHONCHUS
TYPE I
TYPE II

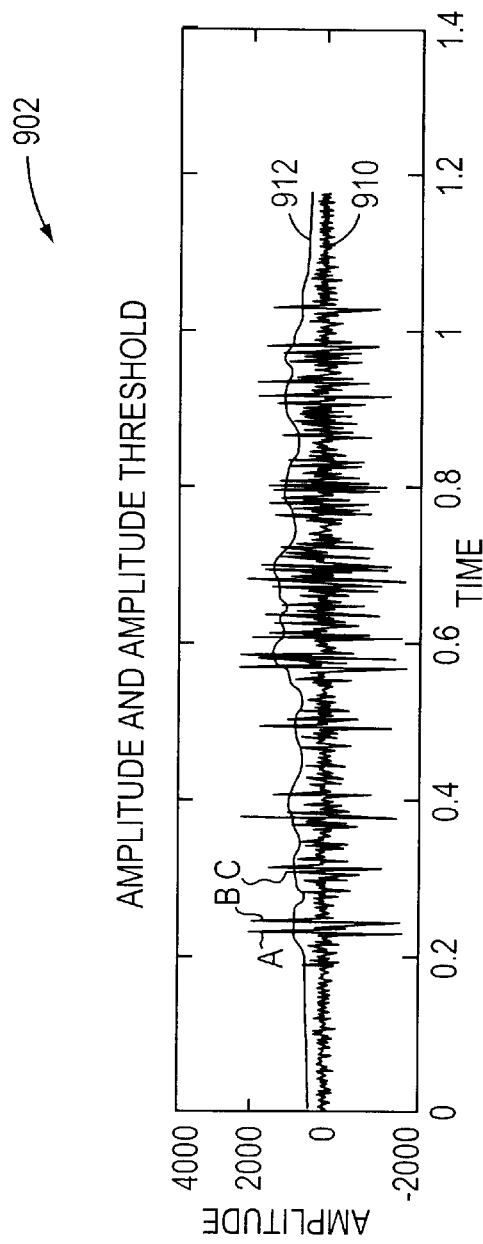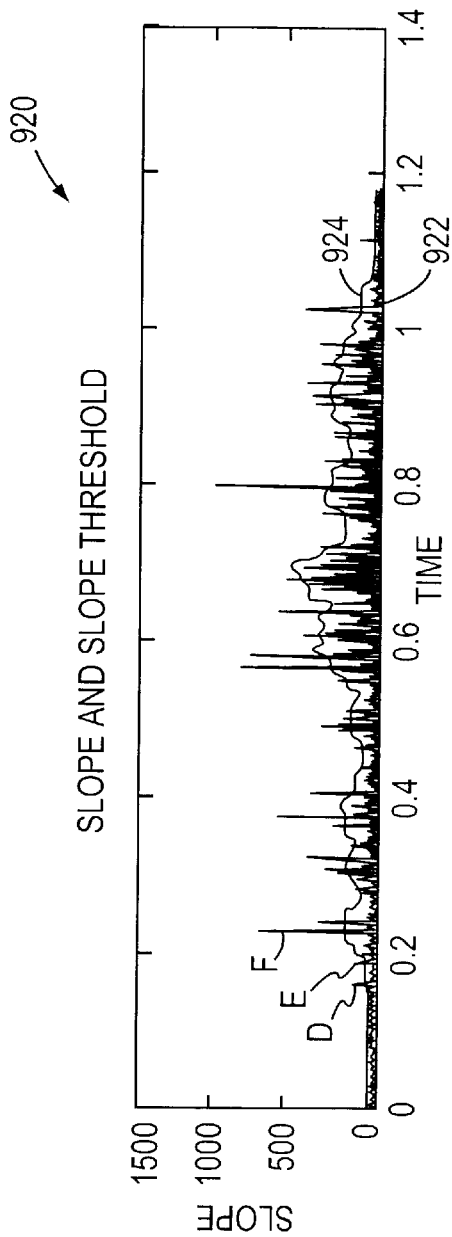

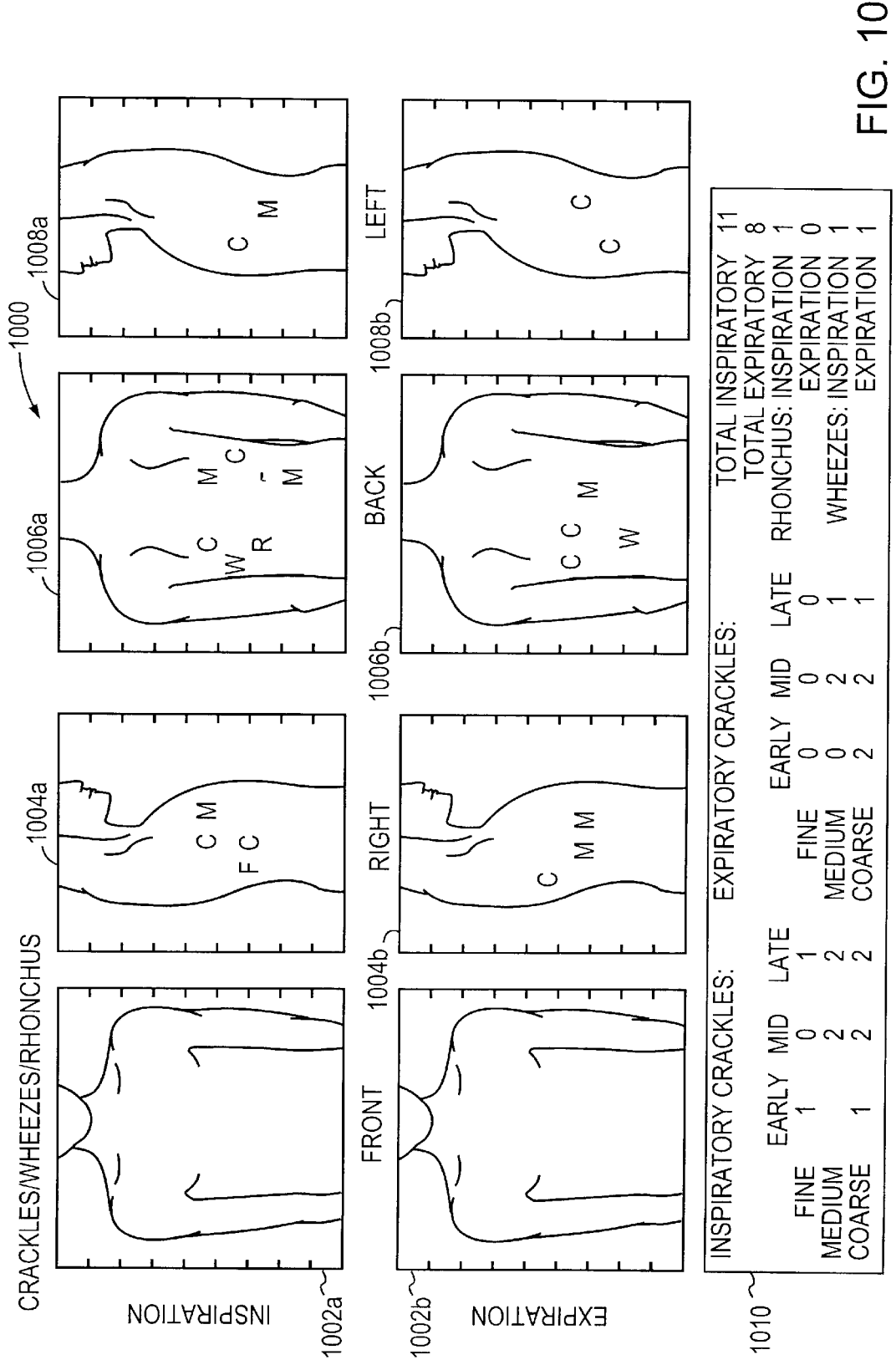

METHOD AND APPARATUS FOR DISPLAYING BODY SOUNDS AND PERFORMING DIAGNOSIS BASED ON BODY SOUND ANALYSIS

This application is a continuation-in-part of application Ser. No. 09/699,546 titled METHOD AND APPARATUS FOR DISPLAYING LUNG SOUNDS AND PERFORMING DIAGNOSIS BASED ON LUNG SOUND ANALYSIS, filed Oct. 30, 2000, now U.S. Pat. No. 6,394,967 which is a continuation of application Ser. No. 09/172,343, filed Oct. 14, 1998, now U.S. Pat. No. 6,139,505.

BACKGROUND OF THE INVENTION

1. Field of the Invention

The present invention relates generally to non-invasive diagnostic systems and techniques, and more specifically, to a method and apparatus for diagnosis based upon the review and analysis of body sounds.

2. Background Information

Since the time of its invention in the early 1800's, the stethoscope has been used routinely by physicians to amplify sounds in the human body. The physician typically places the chest piece of the stethoscope against the patient's skin and listens through the stethoscope's earpieces. By monitoring a patient's breathing, a physician may detect the existence of adventitious (i.e., abnormal and/or unexpected) lung sounds. The identification and classification of adventitious lung sounds, moreover, often provides substantial information about pulmonary and associated abnormalities.

Adventitious lung sounds may be classified into two major types: crackles (or rales), which are discontinuous (i.e., interrupted) sounds, and wheezes and rhonchi, which are continuous. Crackles may be further classified as coarse, medium or fine, depending on their frequency, characteristics and amplitude. Wheezes may be similarly classified as sibilant or sonorous. An experienced and knowledgeable physician, moreover, may be able to diagnose certain pulmonary diseases, such as pneumonia, asthma, etc., simply by detecting, identifying and noting the location of particular adventitious lung sounds.

Lung sounds may also be recorded and displayed to assist in the detection and identification of adventitious sounds. For example, U.S. Pat. No. 3,990,435, entitled BREATH SOUND DIAGNOSTIC APPARATUS to Raymond L. H. Murphy, Jr., the inventor herein, discloses a system for providing a time-expanded visual display of lung sounds. That is, the time scale of the tracing or waveform detected by a microphone, normally plotted at approximately 25–50 mm/sec. by standard medical strip charts, is expanded to approximately 800 mm/sec. Expanding the time scale of the waveform significantly improves the physician's ability to detect and identify adventitious sounds.

Devices to analyze recorded lung sounds are also known. For example, U.S. Pat. No. 5,010,889, entitled INTELLIGENT STETHOSCOPE to Bredesen et al., discloses a stethoscope capable of digitizing and storing body sounds, including heart and lung sounds, in a memory structure configured to store up to six different sounds. The stethoscope includes a single chest piece with a microphone, which may be moved to one of six locations around the patient's chest. The stethoscope further includes a liquid crystal display (LCD) panel for displaying the waveform of a recorded sound.

Using waveform signature analysis, each of the six recorded waveforms is examined to determine the presence of high-pitch sounds which may correspond to fine crackles or low-pitch sounds which may correspond to coarse crackles. The presence or absence of these sounds is then formed into an array that may be compared with pre-recorded arrays corresponding to known conditions, e.g., normal lung sounds, pneumonia, etc. If a match is found between the recorded waveforms and one of the pre-recorded arrays, a diagnosis may be displayed on the LCD panel of the stethoscope.

Although Bredesen's intelligent stethoscope represents an improvement in diagnostic tools, especially for physicians lacking extensive experience in detecting and identifying adventitious lung sounds, it nonetheless has several disadvantages. First, the intelligent stethoscope has only a single microphone, so that obtaining recordings at multiple locations is time-consuming. A single microphone also makes it impossible to record a given sound (e.g., a particular inspiration or expiration) from more than one point on the chest. Second, the small LCD panel is capable of displaying only a single waveform in one predefined format and is provided simply to determine whether valid data has been obtained. Due to these limitations, the intelligent stethoscope is not that likely to provide accurate diagnoses.

SUMMARY OF THE INVENTION

It is an object of the present invention to provide an improved method and apparatus for facilitating the diagnosis of certain diseases based upon recording, review and analysis of body sounds.

It is a further object of the present invention to provide an improved method and apparatus that provides the diagnostician with a richer, more fully coordinated set of data for rapidly and accurately detecting body sound abnormalities.

Another object of the present invention is to provide a system configured to generate graphical displays of detected abnormal body sounds to facilitate diagnosis.

A still further object of the present invention is to provide a system for automatically providing an accurate diagnosis based upon an analysis of recorded body sounds.

Briefly, the invention relates to a system for recording, displaying and analyzing body sounds to facilitate the diagnosis of various diseases. The system includes a plurality of transducers, such as microphones, that may be placed at preselected sites around a patient's chest. The transducers detect the sound or vibration of the body at these sites. The system also includes signal processing circuitry for conditioning and converting analog signals generated by the transducers into digital data. Additionally, the system includes a computer station coupled to the signal processing and digitizing circuitry. The computer station includes a processor, input/output circuitry, a data storage device, at least one input device, such as a keyboard or a mouse, and a graphical user interface. The system may further include a printer. Executing on the computer station is a first application program that collects and organizes the data for display on the graphical user interface and/or for printing.

More specifically, a plurality of transducers are preferably utilized simultaneously to obtain sound information from the patient. In response to the patient's inspiration and expiration, each transducer generates analog signals that are conditioned and digitized by the signal processing circuitry and stored by the computer station at the data storage device. The first application program organizes the received data from all sites for simultaneous display on the graphical user interface and/or printing in multiple time scales preferably in a vertical stack arrangement, such that all of the information may be reviewed concurrently by an attending physician. The first application program may also display the data in frequency versus time format. In addition, by comparing the displayed or printed combinational data with predefined criteria or guidelines, an accurate diagnosis may be reached.

In a further embodiment of the present invention, a second application program, also executing on the computer station, analyzes the data recorded by the transducers. In particular, the second application program preferably includes means for identifying and counting the number and time of occurrence of adventitious sounds, such as wheezes, rhonchi and crackles, and categorizing the identified crackles as fine, medium or coarse. The second application program may also include means for performing other quantitative analysis, such as the ratio of duration of inspiration to expiration and statistical analysis of the intensity of the recorded sounds. This information may then be provided to the attending physician in a variety of ways. For example, it may be displayed in tabular format or graphically in relation to the point on the patient's chest at which the abnormal sound occurred.

A third application for generating a possible diagnosis may also be included. The third application may be a data analysis program, such as a neural network module or a statistical analysis module using multiple logistic regression models, that interoperates with a database of pre-classified lung sounds. Specifically, the database preferably includes multiple data sets for normal lungs sounds and lung sounds associated with specific diseases, such as COPD, asthma, and IPF. The database may be used to train a neural network classifier or to perform a statistical classification. The neural network module analyzes various quantities computed from the patient's lung sounds in view of the training database and, if a match of sufficient reliability is found, presents a preliminary diagnosis and corresponding probability.

A fourth application for automatic localization of the origin of adventitious and normal sounds may also be included. Preferably, the localized sounds are displayed in three-dimensions (3D) using preselected images or glyphs for the corresponding adventitious sounds that have been detected.

In addition, sounds can be input to the patient. These input sounds can then be detected by the plurality microphones disposed around the patient and the information can be displayed and analyzed.

BRIEF DESCRIPTION OF THE DRAWINGS

The above and further advantages of the invention may be better understood by referring to the following description in conjunction with the accompanying drawings, in which:

FIGS. 9A and 9B are data plots that may be generated by the adventitious sound detection application program;

FIG. 10 is a highly schematic illustration of a graphical display showing the points at which abnormal sounds were detected;

DETAILED DESCRIPTION OF AN ILLUSTRATIVE EMBODIMENT

Figure 1:
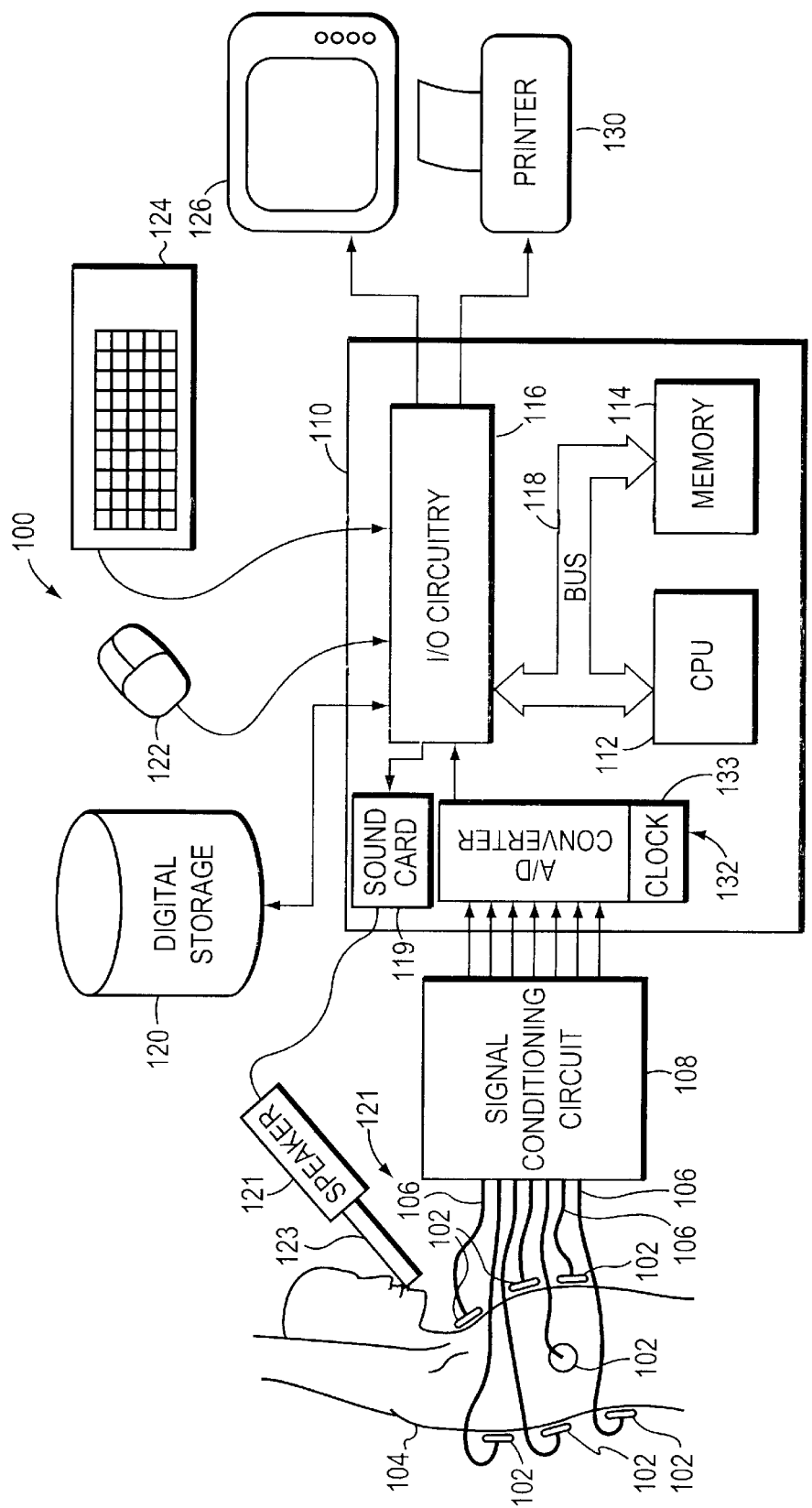
FIG. 1 is a block diagram of a system for implementing a preferred embodiment of the present invention.

FIG. 1 is a block diagram of the lung sound recording and analysis system 100 of the present invention. The system 100 includes a sensor system 101 which includes a plurality of sound transducers, such as analog microphones 102, that may be placed at various sites around the chest or other area of a patient 104. In the preferred embodiment of the invention, the system 100 uses sixteen different sites, of which, fifteen are located around the chest and one is located at the patient's trachea. More specifically, there is one site on the left side, one site on the right side, two sites on the upper front chest separated by the spinal column (proximate to the top portion of the lungs), one site on the lower right front chest, two sites on the upper back (proximate to the top portion of the lungs), four sites in the middle back (proximate to the mid portion of the lungs), four sites at the lower back (proximate to the bottom of the lungs) and one site at the trachea. It should be understood that other chest sites may be utilized by the system 100. Furthermore, a simpler system may use nine sites, eight around the chest and one at the trachea. The eight chest sites may include two on the upper front chest (separated by the spinal column), one on each side and four on the back (two upper and two lower) each pair separated by the spinal column.

Additionally, sixteen microphones 102, one located at each of the sites, are preferably utilized concurrently by the system 100 during the data collection process, although fewer are shown in FIG. 1 for clarity. This allows the data from all sites to be collected concurrently. Nonetheless, a simpler system may utilize one microphone 102 positioned sequentially at the nine or more sites for data collection and the data collection process repeated at each site. To isolate the microphones 102 from external sounds, they may be embedded in the chest pieces of conventional stethoscopes (not shown). The microphones 102 may also be taped or applied with suitable strapping to the patient 104 to prevent dislocation or movement during the data acquisition process.

Leads 106 extending from each microphone 102 are used to connect the microphones 102 to a signal conditioning circuit 108. In general, the signal conditioning circuit 108 modifies the analog audio signals generated by the microphones 102 in order to remove unwanted noise and boost the signal strength for subsequent digitizing. A suitable signal conditioning circuit for use in the present invention is disclosed in U.S. patent application Ser. No. 08/729,272, filed Oct. 10, 1996, entitled "Method And Apparatus For Locating The Origin Of Intrathoracic Sounds," now U.S. Pat. No. 5,884,997, the specification of which is hereby incorporated by reference in its entirety.

It should be understood that the sensor system 101 may utilize other sound transducers besides analog microphones. System 101 may use, for example, digital microphones, one or more lasers configured to scan the selected sites, accelerometers, etc.

The outputs from the signal conditioner 108 (i.e., processed audio signals from each microphone 102) are provided to a computer station 110. The computer station 110, which may be implemented, at least in part, using a personal computer or workstation, includes a central processing unit (CPU) 112 coupled to a memory 114 and input/output circuitry 116 by a bi-directional bus 118. The memory 114 typically comprises random access memory (RAM) for the temporary storage of information, including application programs and an operating system, and read only memory (ROM) for permanent storage of the computer's configuration and basic operating commands. The operating system controls the operations of the CPU 112. The computer station 110 also includes a sound card 119 connected to a speaker 121 for generating output sounds as discussed in more detail below.

The I/O circuitry 116 preferably connects the computer station 110 to a digital storage device 120, such as a disk drive or removable digital storage media, for storage and retrieval of data as described below. The I/O circuitry 116 also connects the computer station 110 to cursor/pointer control and input devices, such as a mouse 122 and a keyboard 124. A window-based graphical user interface 126 and a printer 130 are also preferably connected to the I/O circuitry 116 of the computer station 110. The input/output circuitry 116 preferably contains the necessary hardware, e.g., buffers and adapters, needed to interface with the control devices 122, 124, the graphical user interface 126, printer 130, memory 114 and digital storage device 120.

The computer station 110 may be a personal computer of the IBM® series of computers sold by International Business Machines® or the Macintosh® series of computers sold by Apple Computer Inc. These computers have resident thereon, and are controlled and coordinated by, operating system software, such as IBM OS2®, Microsoft Windows® or Mac OS 9 operating systems. It should be understood that the system 100 may also be implemented on other computer platforms, such as UNIX-based workstations manufactured and sold by Hewlett Packard Co. of Palo Alto, Calif., or hand-held computers, such as those running the Palm or Win CE operating systems, among others.

As mentioned above, the signal conditioning circuit 108 is preferably connected to the computer station 110 such that the processed audio signals from each microphone 102 are received by computer station 110. Specifically, each output of signal conditioning circuit 108 (which preferably corresponds to a particular microphone 102) is connected to an analog-to-digital ("A/D") converter 132 that may be part of the computer station 110. The A/D converter 132 converts the processed analog audio information into a digital data stream. The sampling rate of the A/D converter 132 is preferably greater than 8000 samples per second and the bit rate is preferably greater than eight bits per sample.

Additionally, the A/D converter 132 synchronously pairs a master time signal from a system clock 133 which, for example, may be included in the A/D converter 132 or be internal to the CPU 112 with the digital audio information corresponding to each microphone 102. The master time signal provides a uniform time index to the signals received from the microphones 102. The paired digital-audio/time information associated with each microphone 102 is then forwarded to the digital storage device 120. The A/D converter 132 is preferably a multi-channel, high bandwidth data acquisition printed circuit board, such as those manufactured and sold by Keithley Metrabyte, Inc. It should be understood that the CPU 112, rather than the A/D converter 132, may pair the master clock signal to the digital audio information. It should be further understood that digital transducers, rather than analog microphones, may be utilized. The use of digital transducers would obviate the need for an A/D converter. Although the analog signal is digitized in the preferred embodiment, those skilled in the art will recognize that the analog signal can be used as well.

Figure 2:
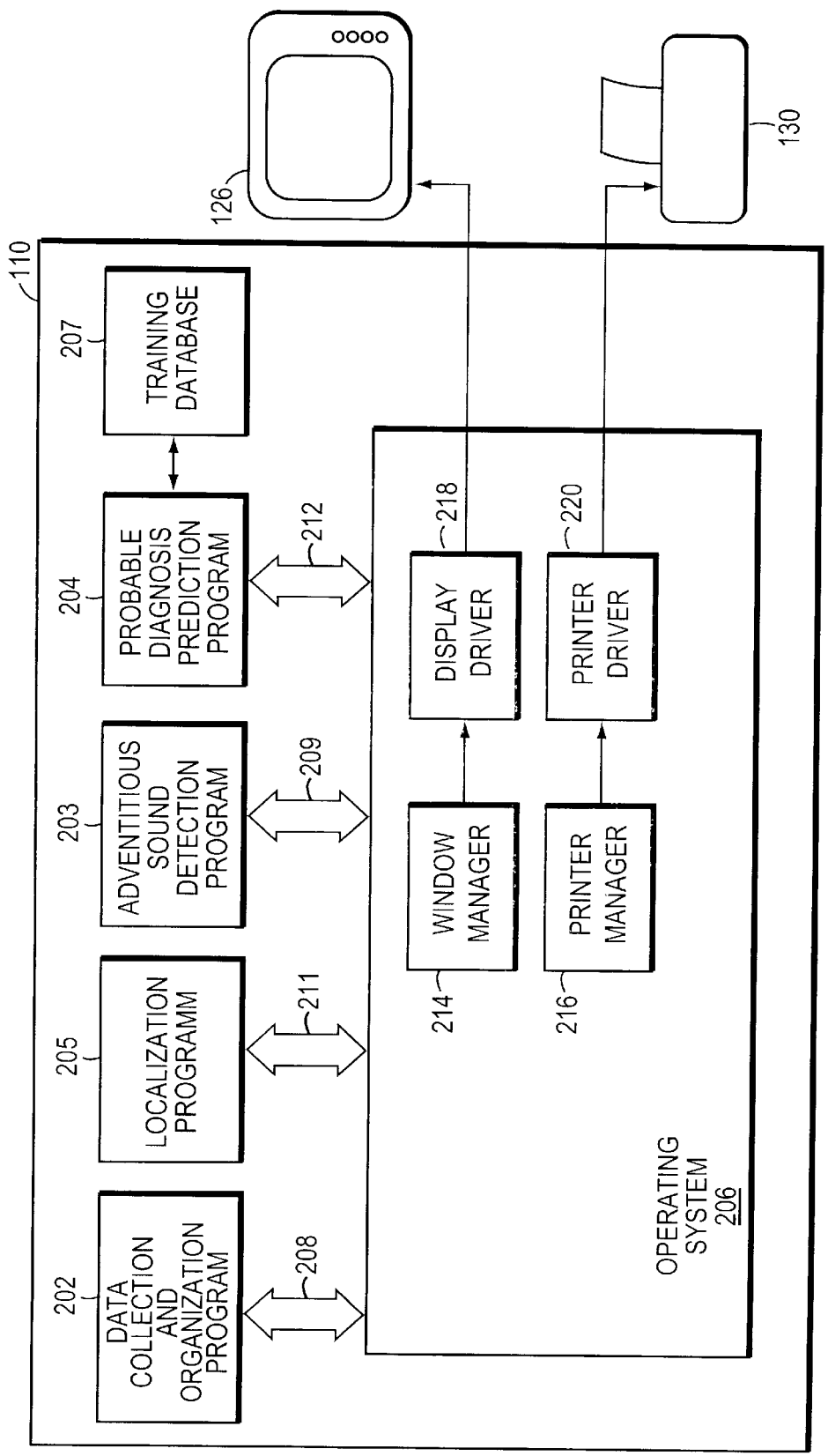
FIG. 2 is a block diagram of the computer station of FIG. 1 illustrating the relationship of an operating system and several application programs.

FIG. 2 is a highly schematized illustration of the computer station 110 illustrating the interaction of several software elements, including a data collection and organization application program 202, an adventitious-sound detection program 203, a probable-diagnosis prediction program 204, an automatic localization program 205, and an operating system 206. The application programs 202–204 execute on the computer station 110. Interacting with the probable-diagnosis prediction program 204, moreover, is a training database 207. The application programs 202–204 and the operating system 206 interact, as shown by arrows 208, 209, 211, and 212, via system calls to control the operations of the computer station 110.

Included within the operating system 206 are system facilities, including a window manager 214 and a printer manager 216, which, inter alia, implement at least some of the system calls. Lower layers of the operating system 206 (or the computer station 110) may also include device drivers, such as a display driver 218 and printer driver 220. Drivers 218, 220 interface directly with hardware components, such as the graphical user interface 126 and the printer 130, respectively.

It should be understood that computer station 110 may include additional application programs. It should be further understood that the computer station 110 may omit the adventitious-sound detection and/or the probable-diagnosis prediction programs 203, 204.

Data Collection and Organization

Figure 3:
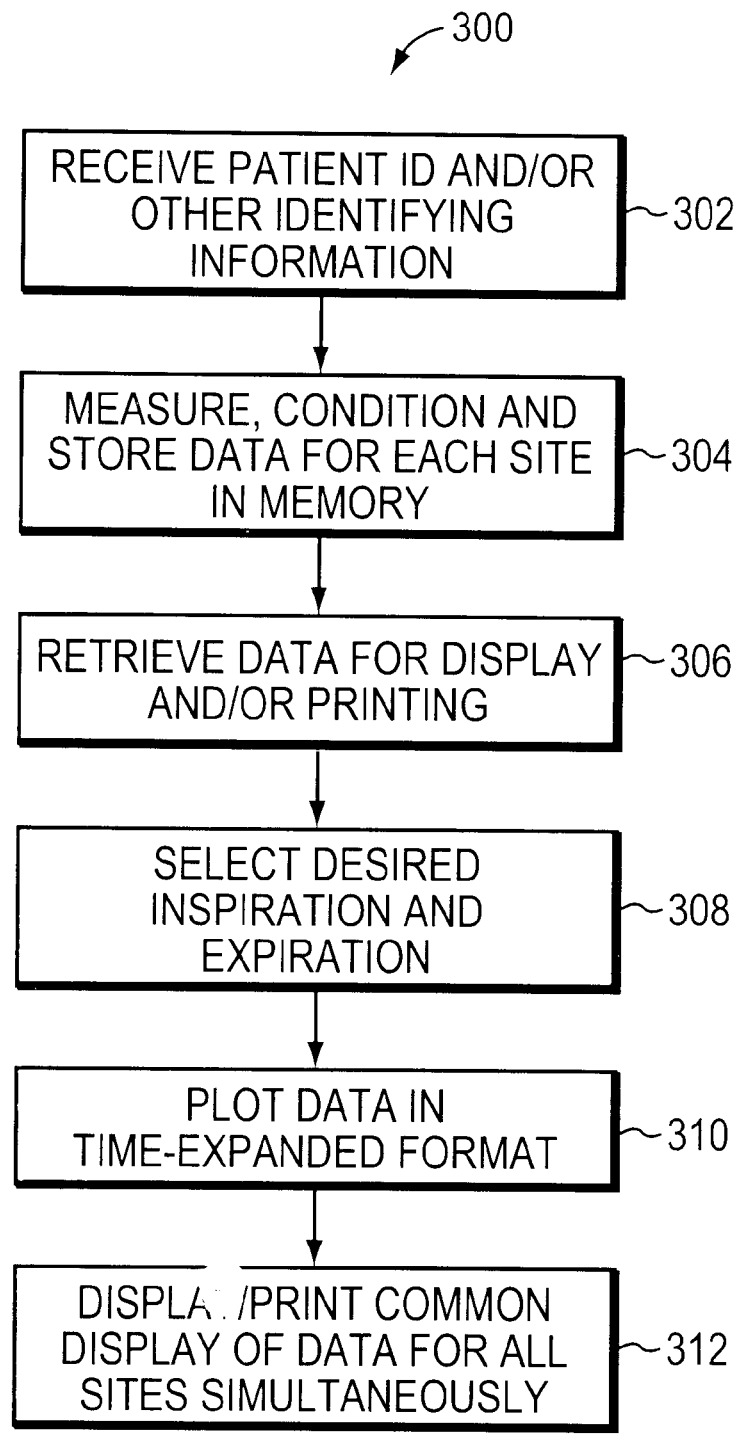
FIG. 3 is a flow diagram of the steps performed by a data collection and organization application program.

In operation, the microphones 102 are preferably taped or strapped to the patient's skin at the sixteen sites. Next, the system 100 is initialized and the data collection and organization application program 202 is preferably opened. FIG. 3 represents a flow chart of operations 300 performed by the data collection and organization application program 202 (FIG. 2). As shown by block 302, the data collection and organization program 202 first requests patient identifying information (such as name, identification number, physician, etc.), which may be entered by a system operator through the keyboard 124 or mouse 122. This information may be displayed on the graphical user interface 126 in a data collection window (not shown). Next, the patient is instructed to breath in (inspiration) and out (expiration) several times. While the patient breathes, lung sounds detected by the microphones 102 are converted to audio signals and provided to the signal conditioning circuit 108. Preferably, data is continuously received for a sufficient period of time (e.g., ten seconds) to ensure that useful data is obtained for at least one inspiration/expiration pair. As indicated at block 304, the audio signals are measured, conditioned and provided to the analog-to-digital converter 132 for digitization. The digital data for each site is then stored at either the memory 114 of computer station 110 or the digital storage device 120. If fewer microphones are used, they may be situated at the next location(s) and the process repeated.

Next, the data collection and organization application program 202 retrieves the data for display or printing, as shown by block 306. Specifically, the data collection and organization application program 202 interacts with the operating system 206 so as to retrieve the data corresponding to each microphone site from memory 114 or the storage device 120. The data for each site, which represents both inspiration and expiration combined, is preferably displayed on screen 228. A preferred form of display is described below.

Figure 4:
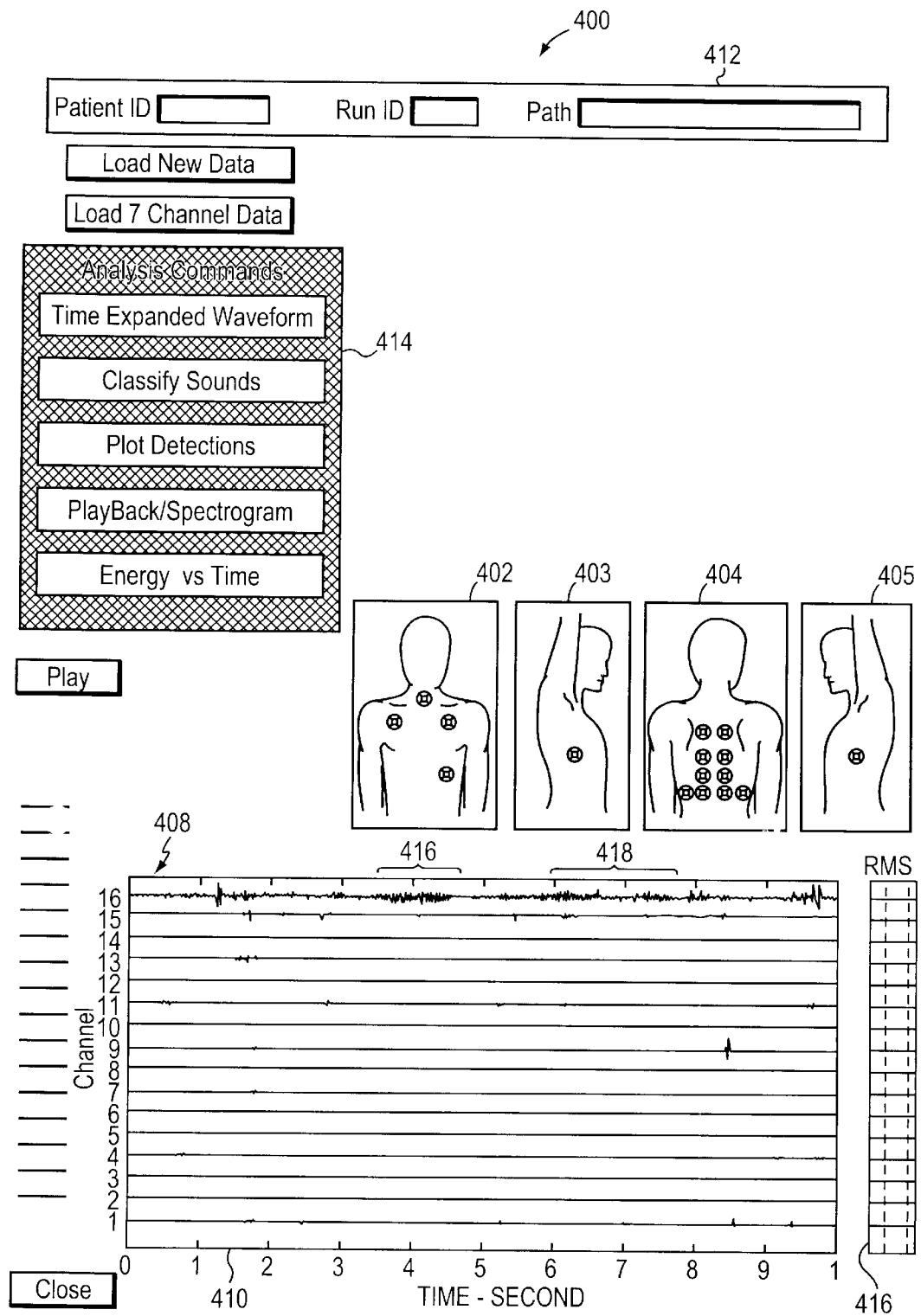
FIG. 4 is a representative display of data for a single location.

As indicated by block 308 (FIG. 3), the system operator then selects a particular inspiration and expiration for further analysis by identifying the corresponding starting and stopping points of the selected inspiration and expiration. Preferably, this is accomplished with the aid of a display formed in accordance with the present invention and illustrated in FIG. 4. FIG. 4 is a highly schematic representation of a preferred display 400 of data obtained from sixteen sites. The display 400 preferably includes a set of body maps 402–405, which illustrate the various sites at which data was recorded, and a data plot area 408, which contains an illustration of the recorded data. More specifically, the data plot area 408 includes the actual data tracings (i.e., signal tracings) obtained at each microphone 102 (FIG. 1) and preferably includes a corresponding time axis 410. The data in data area 408 corresponds to both inspiration and expiration combined and is preferably a plot of signal amplitude (e.g., millivolts or decibels) from the microphones 102, each associated with a particular channel number, versus time in seconds as shown by time axis 410. It should be understood that the display 400 may include other areas, such as a patient data area 412, a command bar area 414 and a root-mean-square (RMS) field 416.

To mark the starting and stopping points of the selected inspiration and expiration, the system operator moves a pointer (not shown) associated with the mouse 122 across the data area 408 to the start of inspiration and executes a mouse "click" at that location, thereby associating a particular time (based on the corresponding point on the time axis 410) with the start of inspiration. The data collection and organization application program 202 preferably includes conventional means to associate the position of the pointer with the time value vertically aligned therewith upon execution of the mouse click. The system operator similarly associates respective times with the end of inspiration and with the starting and stopping times of expiration. The starting and stopping points for inspiration and expiration are best identified by examining the signal or tracing recorded at the trachea microphone (i.e., microphone channel 16). In particular, inspiration is typically associated with a first continuous, high amplitude segment 416 of the trachea signal. When the amplitude of the segment 416 diminishes to near zero, inspiration is typically at an end. Expiration is similarly associated with a continuous, high amplitude segment 418 that directly follows inspiration segment 416. When the amplitude of this second continuous segment 418 diminishes to zero, expiration is typically complete.

It should be understood that the data collection and organization program 202 may as an alternative, or a supplement, to operator selection, include one or more modules or routines that automatically identify the starting and stopping points of inspiration and expiration in a similar fashion.

Following the identification of the starting and stopping points of a selected inspiration and expiration, the data collection and organization program 202 proceeds to organize the corresponding data for display as a function of time. In particular, as indicated by block 310 (FIG. 3), the program 202 preferably plots the data corresponding to each site for both inspiration and expiration in a time-expanded format. Execution of the time expansion function is preferably in accordance with the description set forth in U.S. Pat. No. 3,990,435, which is hereby incorporated by reference in its entirety. Specifically, the data collection and organization program 202 preferably generates two increments of time-expanded data: (i) slightly time-expanded and (ii) fully time-expanded. In particular, the data collection and organization program 202 modifies a copy of the data for each site obtained at step 304 so that it may be displayed or printed in a slightly time-expanded scale (e.g., on the order of 200–400 mm/sec.) and in a fully time-expanded scale (e.g., on the order of 800 mm/sec.) in addition to the more conventional, non-expanded time scale of around 20–50 mm/sec. As block 312 indicates, the data collection and organization program 202 then displays and/or prints-out the data corresponding to inspiration and expiration for each site (which is now maintained in three formats: (i) unexpanded, (ii) slightly time-expanded and (iii) fully time-expanded), in a common display, where it can be viewed in all formats simultaneously. Those skilled in the art will recognize that multiple degrees of expansion can be performed.

Figure 5A:
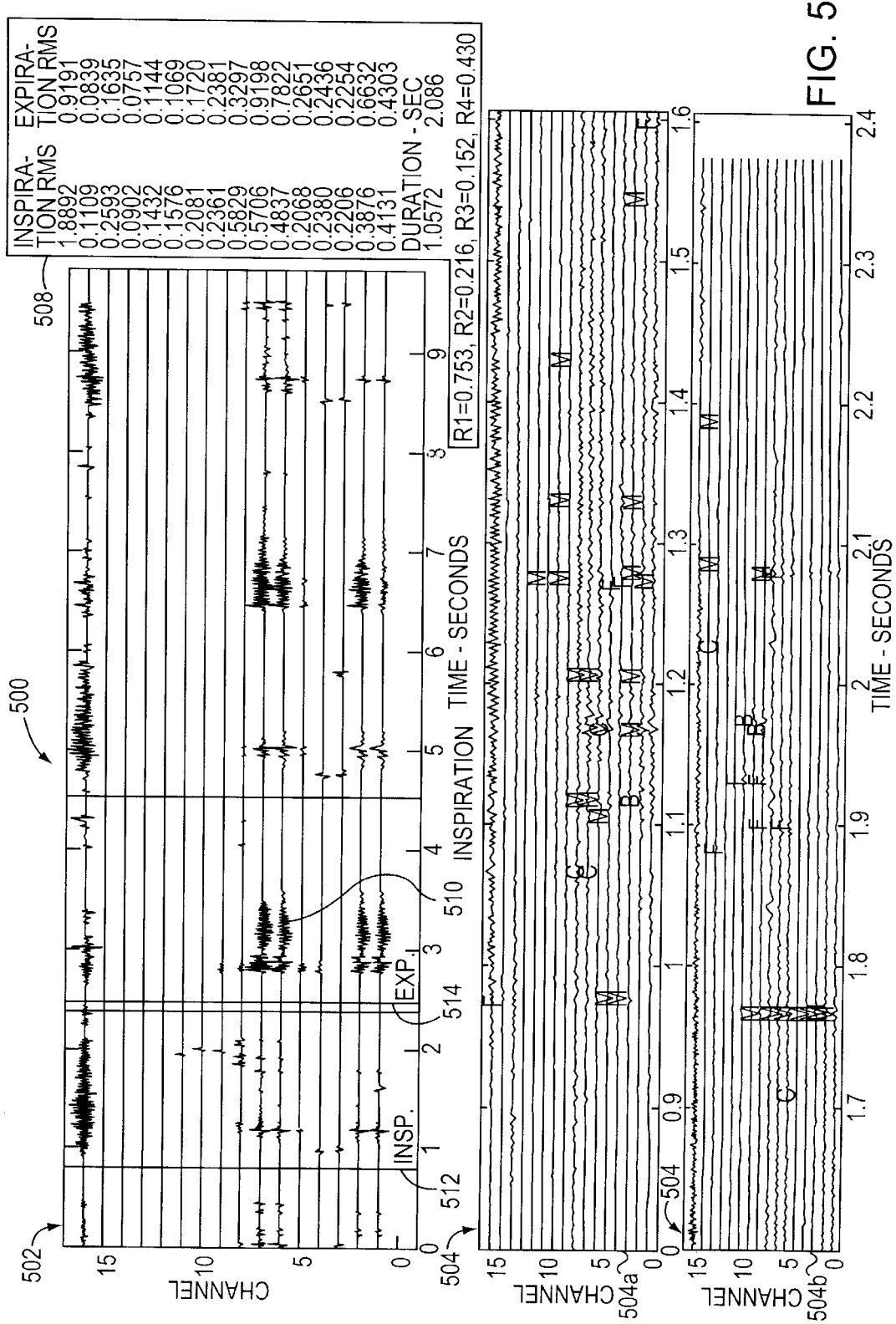
FIGS. 5A and 5B are a highly schematic representation of a combinational display of information.
Figure 5B:
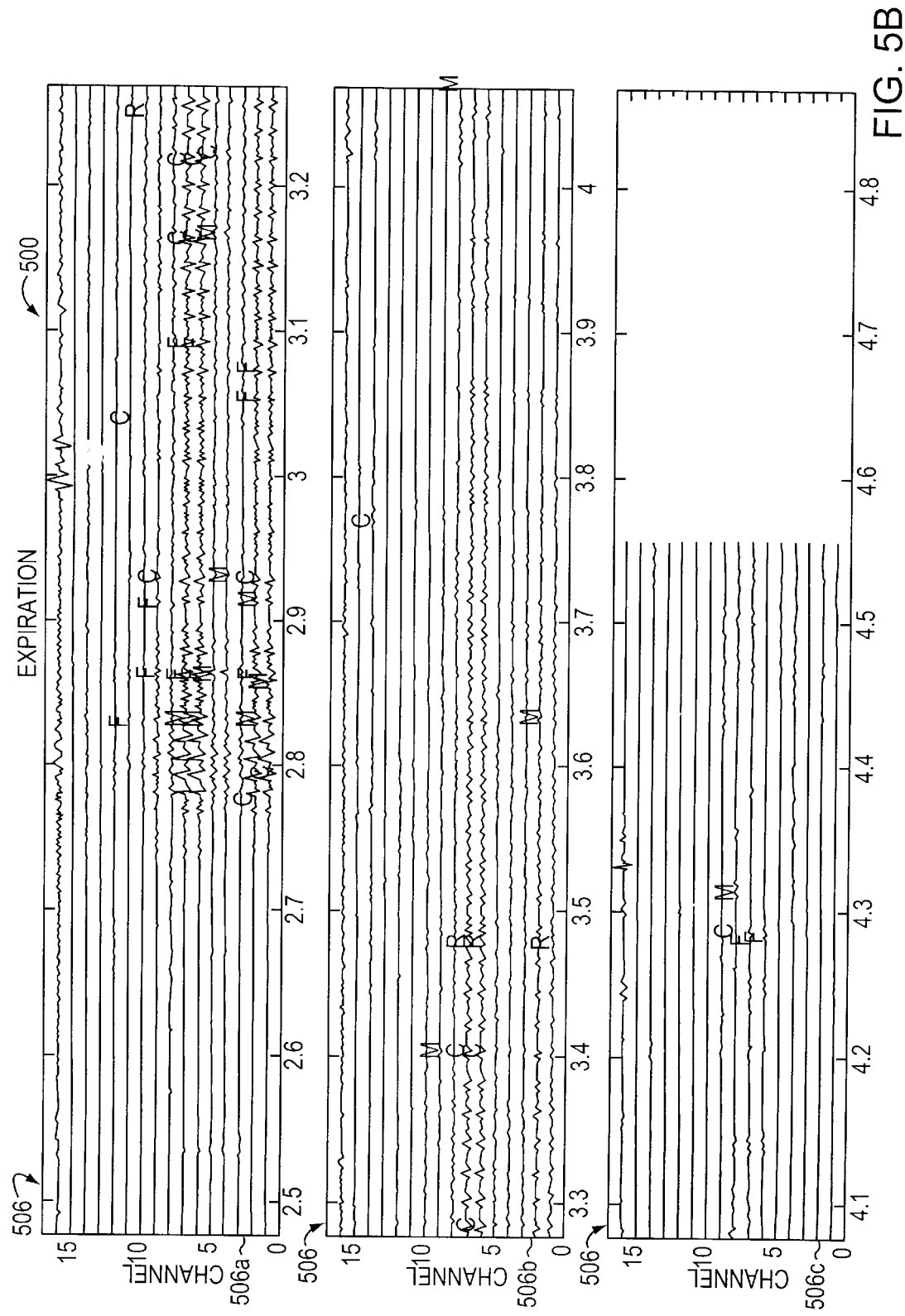

FIGS. 5A and 5B illustrate a highly schematic representation of a preferred combinational display or print-out 500 of lung sound data generated by the data collection and organization program 202. The combinational display 500 includes first, second and third plot elements 502, 504 and 506, respectively, and a data field 508. Each plot element 502, 504 and 506 includes a data or signal trace (e.g., trace 510 in first plot element 502) of the amplitude of the detected lung sounds (vertical axis) for each microphone as a function of time (horizontal axis). As mentioned above, the microphones 102 (FIG. 1) may be identified by channel (e.g., channels one through sixteen) at least one of which (e.g., channel sixteen) corresponds to the patient's trachea. Channels one to fifteen preferably represent the fifteen microphones each located at a different site around the patient's chest, as described above. The first plot element 502 represents the lung sound data for all inspirations and expirations over the predefined time period (e.g., ten seconds) combined in an unexpanded time scale. That is, the data is formatted for display at approximately 20–50 mm/sec. The time period represented by the first plot element 502 is preferably selected so that at least one set of inspiration and expiration data of sufficient quality is obtained. The previously selected inspiration and expiration are preferably enclosed within blocks located in the first plot element 502. In particular, the selected inspiration is enclosed in a first block 512 and the selected expiration is enclosed in a second block 514.

Second plot element 504 represents the lung sounds corresponding to the selected inspiration as detected by each microphone in a slightly time-expanded format. That is, the data is displayed on an approximately 200–400 mm/sec. scale. Depending on the length of the selected inspiration, second plot element 504 may comprise more than one (e.g., two) panels 504a and 504b. Similarly, the third plot element 506 represents the lung sounds corresponding to the selected expiration for each microphone also in a slightly time-expanded format. Since the selected expiration was adjacent to the selected inspiration, the time scale (horizontal axis) for the third plot element 506 continues on from the time scale for the second plot element 504. The third plot element 506 may also be represented by multiple panels, such as panels 506a, 506b and 506c, depending on its length. The signal tracings within the first, second and third plot elements 502, 504 and 506, moreover, are preferably arranged in a vertical stack configuration relative to each other.

The data field 508 preferably includes several computed quantities as determined from the selected inspiration and expiration information. More specifically, the data field 508 preferably contains a root-mean-square (RMS) value calculated in a conventional manner for each channel during the selected inspiration and expiration. The RMS values may be provided in column format adjacent to the first plot element 502. In addition, data field 508 may include the length of time of the selected inspiration 512 and the selected expiration 514, preferably in seconds. Data field 508 may further include other computed statistical quantities identified as R1, R2, R3, R4, R5, R6, R7 and R8, that are of interest to the attending physician.

For example, R1 may represent the ratio of time of selected inspiration to time of selected expiration. R2 may be the ratio of R1 to the average RMS value at the trachea during inspiration. R3 may be the ratio of the average RMS value during inspiration for the microphones located on the chest to the RMS value for the trachea during inspiration. R4 may be the standard deviation of the RMS values during inspiration for all of the channels. R5 may represent the ratio of the mean interchannel non-homogeneity of the start of inspiration to the duration of the inspiration at the trachea. R6 may represent the ration of the mean interchannel non-homogeneity of the end of inspiration to the duration of the inspiration at the trachea. R7 may represent the product of inspiratory sounds root mean square (RMS) averaged between chest sites and the duration of inspiration at the trachea (time integrated amplitude). R8 may represent the ratio of sound energy below 80 Hz to that from 80 Hz to 800 Hz.

In a preferred embodiment, adventitious sounds, such as crackles, are subtracted out of the signal before computation of RMS values. This subtraction operation is preferably performed as crackles can be disproportionately loud, e.g., have much higher amplitudes, in comparison with the rest of the signal, thereby resulting in a calculated RMS value that is not necessarily reflective of regional ventilation.

Once the recorded data has been displayed and/or printed in the manner illustrated in FIGS. 5A and 5B, it is preferably reviewed by the attending physician. As shown, the combinational display 500 concisely and effectively presents the data obtained at multiple sites to the attending physician. In particular, examination of plot elements 504 and 506, which represent the slightly time-expanded data, quickly reveals the occurrence of any adventitious sounds. Further review of these elements 504 and 506 provides detail information regarding the existence, identity and location of the adventitious sounds. For example, by simply referring to the corresponding channel number, a physician may quickly ascertain at which location an adventitious sounds was recorded. By arranging the signal tracings in a vertical stack as shown in the combinational display 500, he or she may also judge whether the same event produced adventitious sounds detected at more is than one location. This may all be performed, moreover, without having to switch back-and-forth between a plurality of screens or sheets. That is, the data collection and organization application program 202 (FIG. 2), in cooperation with the operating system 206, may adjust the size of the plot elements 502, 504 and 506 so that they fit in their entirety in one or two windows on the display screen 228 or on one or two sheets of paper, if printed. Moreover, the system 100 may mark the location of detected adventitious sounds within the second and third plot elements 504 and 506, utilizing a set of abbreviations as identifiers, as described below. For example, "C" stands for a coarse crackle, "M" stands for a medium crackle, "F" for a fine crackle, "W" for a wheeze and "R" for rhonchi.

By comparing the data contained within combinational display 500 with information indicative of various pulmonary conditions or diseases, moreover, the physician may be able to render a diagnosis with a relatively high degree of accuracy. In particular, Table 1 lists the criteria or characteristics of lung sounds associated with four possible conditions: normal, COPD, asthma and IPF, based on empirical studies and analysis of numerous subjects with the indicated conditions. As shown in Table 1, for example, a normal patient's expiration should last about 20% longer than his inspiration. This information, moreover, may be quickly obtained by simply reviewing the R1 value in the data field 508. For a patient suffering COPD, expiration is typically on the order of 60% longer than inspiration.

TABLE 1

CHARACTERISTICS OF PULMONARY SOUND TRACINGS

|  | Normal | COPD | Asthma | IPF |
| --- | --- | --- | --- | --- |
| Ratio of Time of Inspiration to Time of Expiration | Expiration 20% longer than Inspiration (on average) | Expiration 60% longer than Inspiration (on average) | Expiration typically much longer than Inspiration | variable |
| Distribution of Sounds over the Patient's Chest | Relatively high amplitude of sounds during Inspiration, little or no variation in sound amplitude across the chest | Amplitude of sounds during Inspiration variable, but higher than amplitude of sounds during Expiration | Relatively uniform distribution of sounds across the chest, wheezes typically present | variable |
| Sounds Occurring During Inspiration | appear random | broken, irregular | wheezes typically present | crackles typically present |
| Occurrence of Abnormal Sounds During Inspiration and Expiration | few | wheezes and rhonchi typically present, early inspiratory crackles also common | prominent wheezing, rhonchi may also be present | many crackles typically present |

Figure 6A:
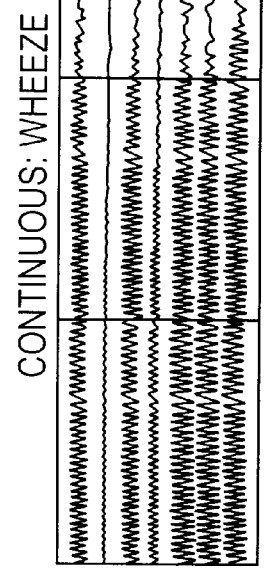
FIGS. 6A–C are exemplary plots of lung sound data versus time illustrating the appearance of several adventitious sounds.
Figure 6B:
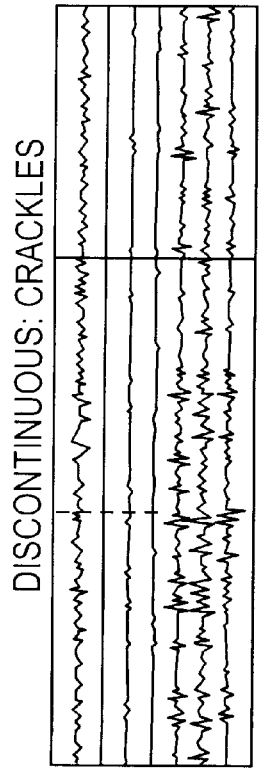
Figure 6C:
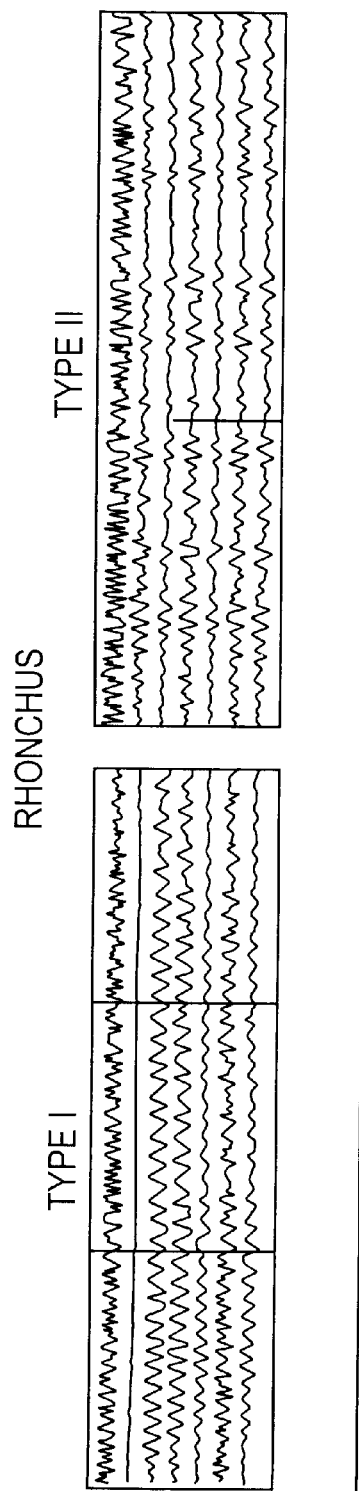

A diagram of illustrative adventitious or abnormal sounds may also be utilized by the attending physician, in combination with the information contained in Table 1, when reviewing combinational pulmonary display 500 so as to assist in arriving at a diagnosis. FIG. 6A is an exemplary plot of lung sound amplitude (vertical axis) versus time (horizontal axis) for a plurality of microphones illustrating the appearance of crackles. FIG. 6B is a similar exemplary plot illustrating the appearance of a wheeze. FIG. 6C is another exemplary plot illustrating the appearance of Type I and Type II rhonchus.

The preferred combinational display thus portrays the detected sounds so that the presence or absence of the characteristics specified in Table I may be ascertained. In particular, the combinational display portrays the following information: (1) the ratio of inspiration to expiration, preferably as a percentage; (2) the distribution of adventitious sounds over the chest and their relative amplitudes; (3) the occurrence of adventitious during inspiration and expiration; and (4) whether the adventitious sounds are crackles, wheezes or rhonchi. As shown, the preferred display 500 provides all of this information to the attending physician in a coherent, efficient manner.

Figure 7:
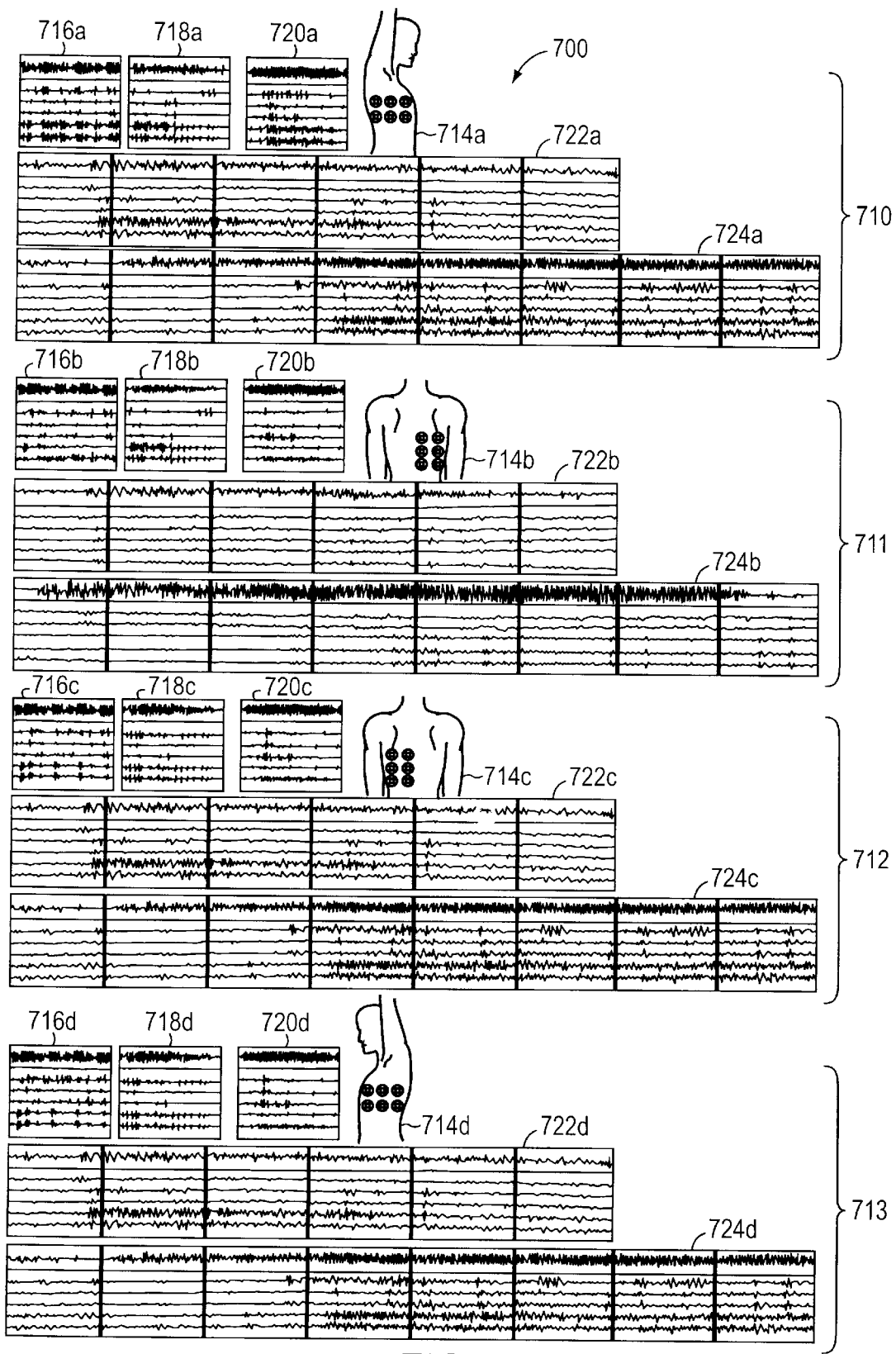
FIG. 7 is a highly schematic representation of another combinational display of information.

Nonetheless, it should be understood that other combinational displays may be generated by the system. For example, FIG. 7 is a highly schematic representation of another combinational display or print-out 700 of data by the data collection and organization program 202 (FIG. 2) from block 312. As shown, data from four chest regions (right is back, left back, right side and left side) is simultaneously portrayed either on the graphical user interface 128 and/or printed preferably on a single sheet of paper from printer 130. The combinational display 700 is preferably divided into four sections 710–713, each corresponding to a particular chest region at which data was obtained. Within each section 710–713, moreover, may be a graphical body illustration 714a–714d, corresponding to the particular chest region at which the respective data was obtained. For example, graphical illustration 714b, associated with the data in section 711, corresponds to the patient's right back region.

Each section 710–713 preferably includes a representation of the data in multiple time scales and formats. In particular, a first display element 716a–716d, disposed with each section 710–713, respectively, illustrates the data obtained at each microphone for several repetitions of inspiration and expiration combined in an unexpanded time scale. That is, the data is formatted for display at approximately 20–50 mm/sec. A second display element 718a–718d, similarly disposed within each section 710–713, respectively, illustrates the data obtained at each microphone for inspiration only in a slightly expanded scale (e.g., on the order of approximately 200–400 mm/sec.). A third display element 720a–720d illustrates the data obtained by each microphone during expiration only, also in a slightly expanded scale (e.g., on the order of approximately 200–400 mm/sec.).

A fourth display element 722a–722d illustrates inspiration only for each microphone in a fully expanded time scale. That is, the data is displayed on an approximately 800 mm/sec. scale. A fifth display element 724a–724d, corresponding to each section 710–713, respectively, illustrates the data for expiration only, also in a fully expanded scale. In the preferred embodiment, the first through third display elements (i.e., elements 716, 718 and 720) are all preferably arranged side-by-side above display element 722. Additionally, display element 724 corresponding to fully expanded expiration, which is often the longest, is preferably arranged below display element 722 and may wrap around as necessary.

Other arrangements of the display elements 716–724 forming combinational display 700 may also be employed. Nonetheless, all of the display elements 716–724 are preferably arranged so as to be shown simultaneously. That is, all of the display elements 716–724 are preferably arranged to appear on the graphical user interface 128 at the same time and/or printed on a single sheet of paper.

To ensure that the display elements 716–724 of combination pulmonary display 700 are placed on the graphical user interface 128 at the same time and/or preferably printed on a single sheet of paper, the data collection and organization application 202 (FIG. 2), in cooperation with the operating system 206, may adjust the size of the display elements 716–724 so that they will fit in their entirety either on the graphical user interface 128 or on a sheet of paper. Nonetheless, the relative relationships between unexpanded, slightly time-expanded, and fully time-expanded are preferably maintained.

The arrangement of information within the combinational display 500 or 700 facilitates various disease diagnosis by highlighting their distinctive and identifying characteristics to the attending physician. In addition, the above-described procedure, unlike x-rays or exploratory surgery, presents little risk or discomfort to the patient.

Figure 12:
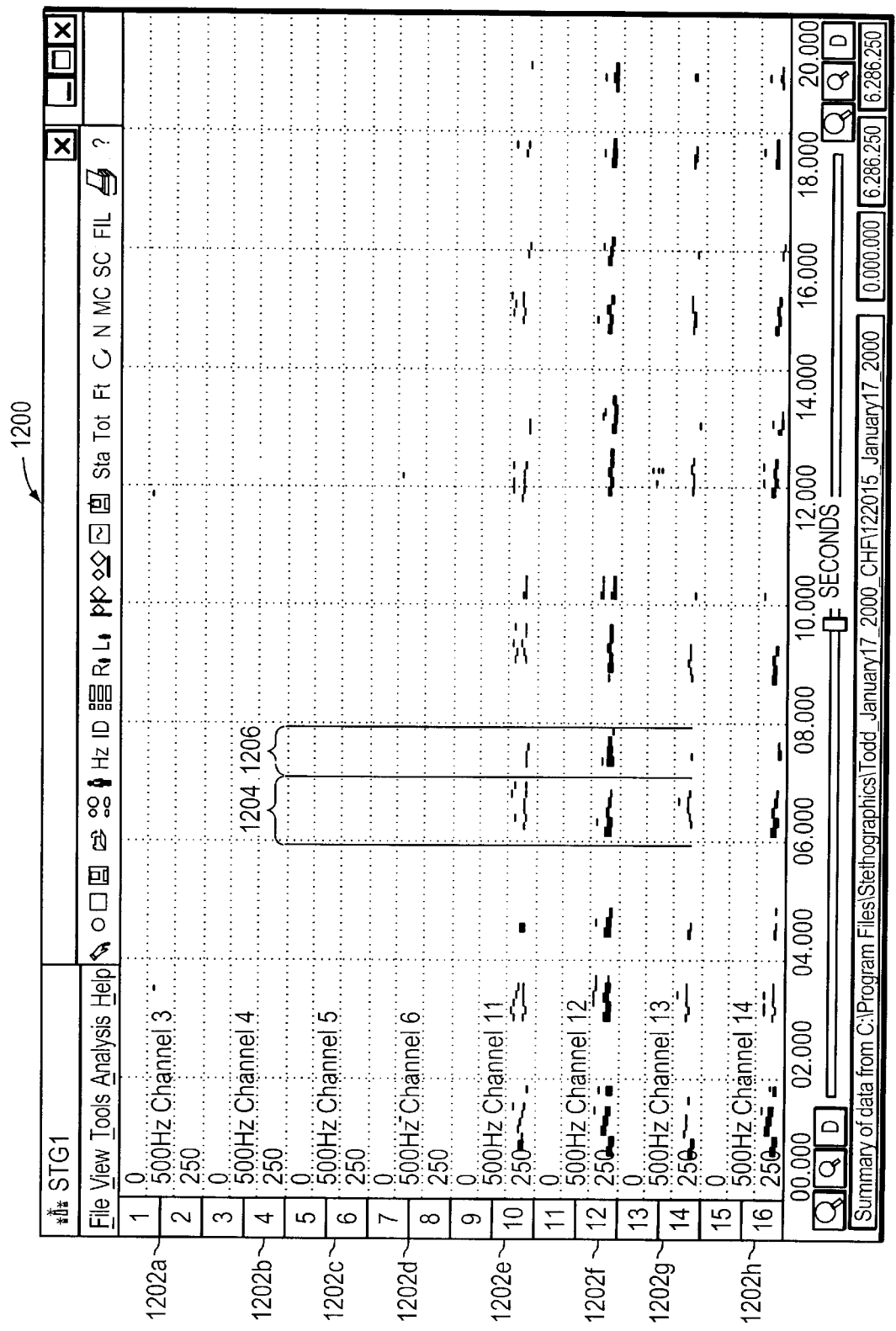
FIGS. 12 and 13 are exemplary displays of lung sound data in frequency versus time format.
Figure 13:
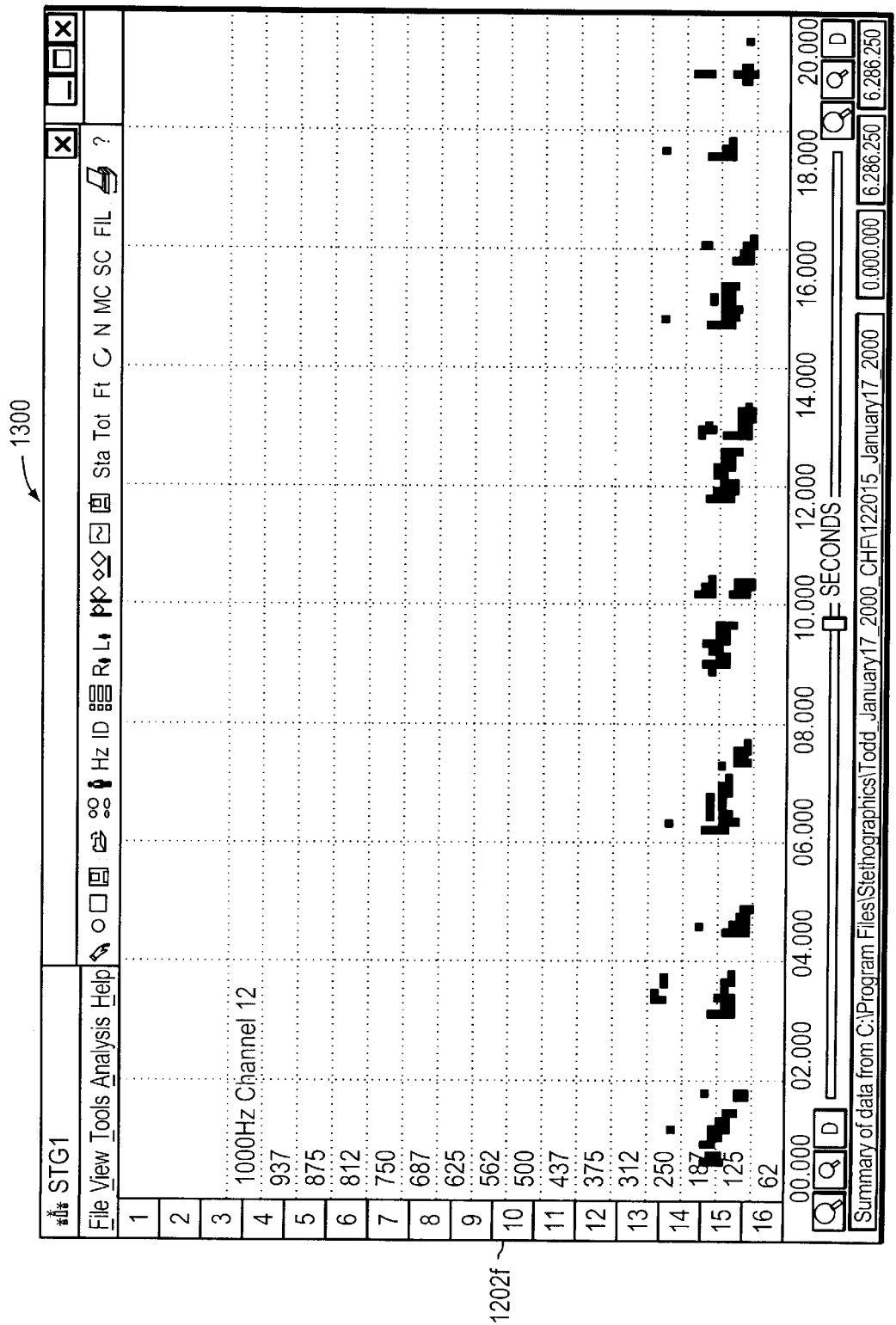

The data collection and organization program 202 may also display body, e.g., lung, sounds recorded from all or a portion of the sixteen microphones 102 in power versus frequency and time, as shown in FIGS. 12 and 13. FIG. 12 illustrates a display or spectrogram 1200 for eight microphone channels 1202a–h where time is on the horizontal axis, frequency is on the vertical axis and signal power is shown by color and/or color intensity. The frequency range for each microphone channel is 0 to 500 Hz. Nonetheless, those skilled in the art will recognize that other ranges may be displayed. The display 1200, which extends for 20 continuous seconds, shows a plurality of inspirations and expirations by the patient. An exemplary expiration is designated generally 1204 and an exemplary inspiration is designated generally 1206. The intensity of sound at the particular frequency and time may be indicated by color. The colors preferably range from light yellow for low sound intensity to dark red for high sound intensity. An attending physician can identify abnormal sounds by simply reviewing the spectrogram 1200. For example, a wheeze can be identified as a continuous high intensity band (dark red) at about 125 Hz as seen in channel 1202f (i.e., channel 12).

FIG. 13 is a display or spectrogram 1300 of a single channel, i.e., channel 1202f, corresponding to the same time period as FIG. 12. Here, the frequency range shown on the vertical axis is 0 to 1000 Hz. The display 1300 thus illustrates the frequencies in greater detail. It should be understood that the data collection and organization program 202 may provide one or more drop down menus or buttons on the display screen 126 for selecting the desired display format, e.g., number of microphone channels, range of time, frequency range, etc.

Adventitious-Sound Detection

In a preferred embodiment, the computer station 110 (FIG. 2) further includes an adventitious-sound detection program 203, as mentioned above. The adventitious-sound detection program 203 preferably parses the data recorded by each microphone 102 (FIG. 1) to identify the occurrence of any adventitious sounds, such as crackles, wheeze or rhonchi. The adventitious-sound detection program 203 preferably operates in accordance with the methods and procedures described in U.S. patent application Ser. No. 406,152, titled LUNG SOUND DETECTION SYSTEM AND METHOD, now U.S. Pat. No. 5,165,417, to Raymond L. H. Murphy, Jr., the inventor herein, which is also incorporated by reference herein in its entirety.

More specifically, the consecutive waves of each sound signal are preferably analyzed to determine when a particular wave meets established predefined amplitude and cycle period criteria. Once such a wave is identified, the next adjacent waves are similarly analyzed to determine whether they meet other predefined cycle period and/or amplitude criteria. Depending on the number of consecutive waves that are found to meet particular period and/or amplitude requirements, the adventitious sound detection program 203 may categorize these portions of the signal as crackles, wheeze, rhonchi, or other adventitious sound, depending on the criteria that were utilized in setting the thresholds.

Figure 8:
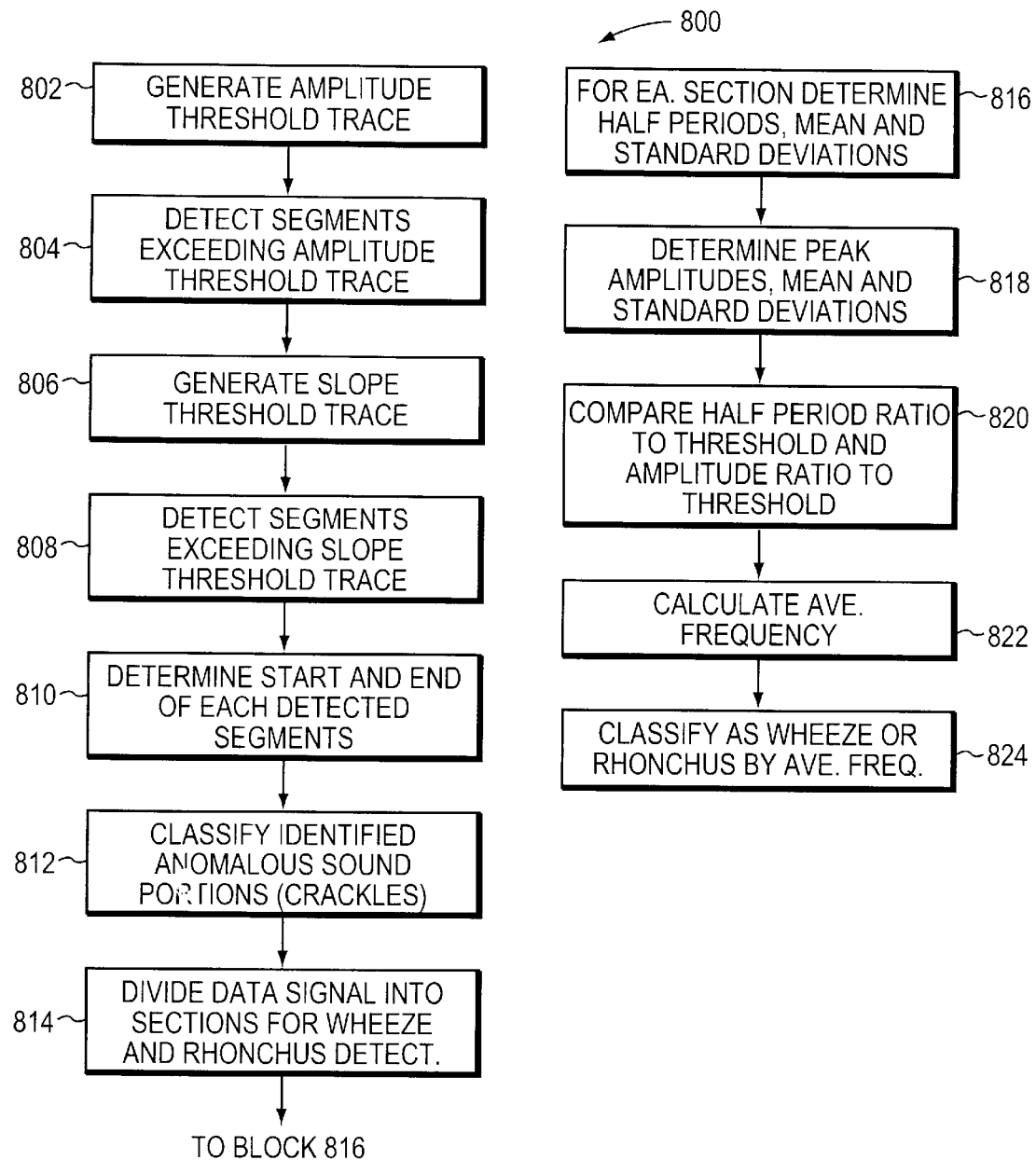
FIG. 8 is a flow diagram of the steps performed by an adventitious sound detection application program.

For example, FIG. 8 is a flow chart of operations 800 executed by the adventitious-sound detection program 203. At block 802, the program 203 first generates a corresponding amplitude threshold trace for the data signal (i.e., signal trace) corresponding to each microphone site. To generate the amplitude threshold trace, the program 203 first determines a running average amplitude trace corresponding to the absolute value of the signal over 600 data points (e.g., 300 data points on either side of the data point for which the running average is currently being calculated). As described above, information from the microphones 102 is preferably sampled at 8000 data points per second. The program 203 proceeds to determine the mean of the running average amplitude trace which is then multiplied by an amplitude threshold constant (e.g., 1.5). The amplitude threshold constant is used to distinguish adventitious sounds, such as crackles, from background lung noise. Empirical studies have shown that an amplitude threshold constant of 1.5 is adequate to distinguish crackle events in most cases, although other values may also be employed. The resulting value is added to the running average amplitude trace to form an amplitude threshold trace.

FIG. 9A is a data plot 902 for a particular microphone 102 (FIG. 1) which represents either inspiration or expiration plotted as a function of time. The data plot 902 includes a data signal 910 and a corresponding amplitude threshold trace 912, generated as described above. As shown, the data signal 910 exceeds the amplitude threshold trace 912 at various points (e.g., points A, B, C, etc.). The adventitious-sound detection program 203, at block 804 (FIG. 8), next compares the data signal 910 (FIG. 9A) to the corresponding amplitude threshold trace 912 and, for each portion of the data that exceeds the corresponding threshold, stores a corresponding index or identifier of that portion of the data.

Next, program 203 similarly identifies portions of the data signal that exceed a signal slope threshold. Specifically, the program, at block 806 (FIG. 8), generates a corresponding slope threshold trace. More specifically, the program 203 calculates the first difference of the data trace using a difference equation. A preliminary slope threshold trace is then formed by calculating the running average over 600 data points. The median of the preliminary threshold trace is then determined and the median is multiplied by a slope threshold constant (e.g., 0.15). The slope threshold constant is chosen to distinguish adventitious sounds from discrete sound artifacts (such as machine noise, skin noises, etc.) that may be present in the signal trace and may also have rapidly rising slopes. Again, empirical studies have shown that a slope threshold constant of 0.15 is adequate in most cases to distinguish adventitious sound events from sound artifacts. The resulting value is then added to the preliminary threshold trace to form a slope threshold trace.

FIG. 9B is a data plot 920 for a particular microphone 102 (FIG. 1) plotted as a function of time. The data plot 920 includes a slope data signal 922 and a corresponding slope threshold trace 924, generated as described above. As shown, the slope data signal 922 exceeds the slope threshold trace 924 at various points (e.g., points D, E, F, etc.).

Returning to FIG. 8, the adventitious-sound detection program 203, at block 808, next compares the slope data signal 822 (FIG. 9B) to the corresponding slope threshold trace 924 and, for each portion of the signal that exceeds the corresponding threshold, stores a corresponding index or identifier of that portion of the signal. Program 203 next proceeds to determine the start and end of each "anomalous" signal segment detected in steps 804 and 808 above. In particular, as shown at block 810, for each segment of the data trace that exceeded the amplitude threshold trace, program 203 may define the end as the first zero crossing after the last point at which the amplitude threshold was exceeded. To determine the start, program 203 preferably locates the earliest slope exceeding point that occurs before the first amplitude exceeding point and defines the start as the zero crossing before the located slope exceeding point. If no corresponding slope exceeding point is found, the portion is not considered to be a crackle event.

After identifying the start and end of each anomalous signal segment within a given signal, program 203, at block 812, is ready to further analyze and classify the various signal segments. In particular, program 203 may first determine the number of zero crossings that are present in the subject anomalous signal segment. If the number of zero crossings is greater than 4 but less than 8, program 203 next proceeds to calculate the first three half periods of the signal portion and computes an average detection width as the mean of the three half period values. If the third half period is longer than the second half period, then program 203 preferably classifies the sound portion as a crackle. Other criteria may optionally or additionally be used to classify sound segments as crackles. For example, a crackle may be defined as having an initial deflection width or a maximum deflection width that exceeds a predefined threshold or a number of sequential deflection widths that exceed some threshold. Additionally, if the computed average detection width (or the initial or maximum deflection widths) is between 0.0015 and 0.0025 seconds, the sound portion is classified as a fine crackle. If the computed average detection width is between 0.0025 and 0.0035 seconds, the sound portion is classified as a medium crackle and if the average detection width is between 0.0035 and 0.0045 seconds, the sound portion is classified as a coarse crackle.

To identify wheezes and rhonchi, program 203 preferably proceeds as follows. First, as shown at block 814, program 203 divides the inspiratory or expiratory data signal corresponding to each site into sections, which may each be ⅛ second in duration. Next, at block 816, program 203 determines all half periods of the zero crossings of the signal, and the mean and standard deviations of the half periods for each section. Similarly, at block 818, program 203 determines the peak amplitudes of each half cycle and the mean and the standard deviation of the peak amplitudes for each segment. These measured half periods and peak amplitudes are then compared to predefined criteria.

As indicated by block 820, if the ratio of the standard deviation of half period to mean half period is less than a predefined threshold (e.g., 0.4) and, if the standard deviation of peak amplitude over mean peak amplitude is less than another predefined threshold (e.g., 0.4), the subject segment is classified as a wheeze or rhonchus. To differentiate between wheezes and rhonchi, program 302, at block 822 calculates the average frequency of the segment (i.e., 1/{2*mean half period}) and, at block 824, compares the average frequency to a predefined threshold (e.g., 200 Hz). In particular, if the average frequency is less than the predefined threshold, program 203 classifies the segment as a rhonchus. If the average frequency is greater than 120 Hz, program 203 classifies the segment as a wheeze.

It should be understood that some other predefined threshold may be used to classify an abnormal sound segment as a rhonchus, e.g., a selected frequency between 100–200 Hz, such as 120 Hz.

It should be understood that other detection algorithms or techniques may be implemented by the system 100.

For example, a database of templates corresponding to various adventitious sounds may be stored in the memory 114 of the system. Portions of the data signal 910 can then be compared to each of the templates until a match is found.

Alternatively, program 203 may be configured to look first at segments exceeding the slope threshold (e.g., start with blocks 806 and 808) and then perform amplitude analysis of blocks 802 and 804. Program 203 could also be configured to filter out the low frequency (e.g., below 600 Hz) portion of the detected signals and designate any remaining segments as fine crackles.

Following the detection of adventitious sounds as described above, the system 100 may display the results to the system operator and/or the attending physician. For example, the system 100, through adventitious sound detection program 203, may label sections of the signals contained in the second and third plot elements 504 and 506 (FIGS. 5A and 5B) at which adventitious sounds were detected. In particular, the system 100 may mark the location of detected adventitious sounds, utilizing a set of abbreviations as identifiers. For example, "C" stands for a coarse crackle, "M" stands for a medium crackle, "F" for a fine crackle, "W" for a wheeze and "R" for rhonchi.

The system 100 may also generate additional body plots either on graphical user interface 128 or in print form to illustrate the location of the detected adventitious sounds. FIG. 10 is a highly schematic illustration showing the location of detected crackles, wheezes, and/or rhonchi. Specifically, a graphical depiction 1000 preferably includes a set of body plots 1002a–1008a for inspiration and a similar set of body plots 1002b–1008b for expiration. In particular, the body plots preferably correspond to a patient's front 1002, right side 1004, back 1006 and left side 1008 chest regions. Again, utilizing a set of abbreviations as identifiers, the system 100 marks the location of detected adventitious sounds.

In addition to the body plots, the graphical depiction 1000 may also include a summary field 1010. Located within the summary field 1010 may be information relating to the total number of fine, medium, and coarse crackles that were detected for inspiration and expiration. The number of crackles may be further defined as having occurred early (e.g., first third), mid (e.g., middle third) or late (e.g., last third) of either inspiration and expiration as a function of time. Similarly, the total number of wheezes and rhonchi that were detected during inspiration and expiration may also be provided within the summary field 1010 of graphical depiction 1000.

Figure 11:
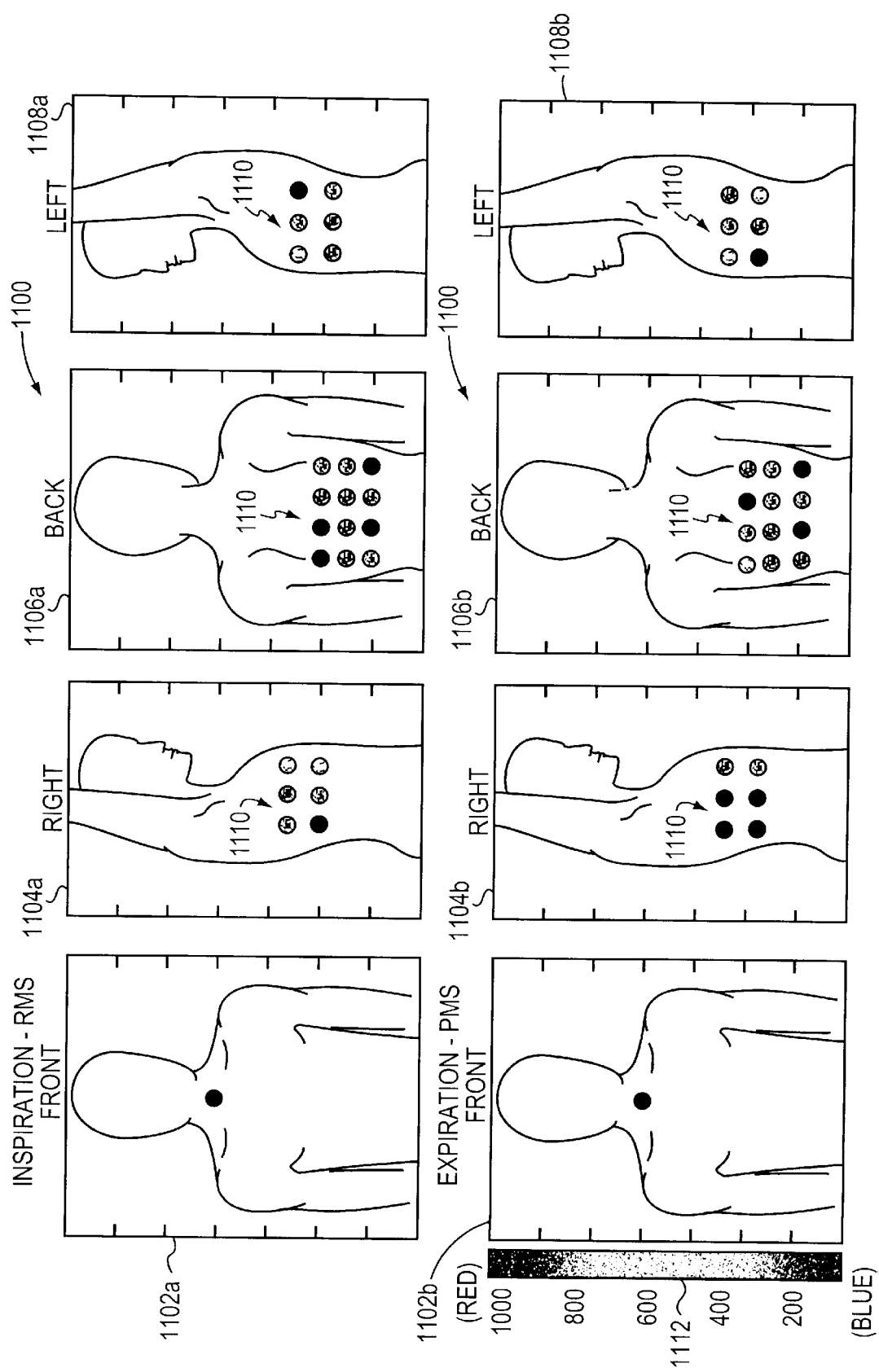
FIG. 11 is a highly schematic illustration of a graphical display showing sound intensity levels as determined by the present invention.

As mentioned above, application program 203 may further determine a root-mean-square (RMS) level for the inspiratory and expiratory portion of the signal from each microphone. The RMS levels provide the attending physician with a mechanism for comparing the intensity of the lung sounds as recorded at each microphone. The computed RMS values, moreover, may be displayed on graphical user interface 128 (FIG. 1) in tabular or graphical form. Referring to FIG. 11, program 203 preferably generates an RMS graphical display 1100 having a first set of body plots 1102a–1108a each corresponding to a particular chest region (e.g., front, right, back and left) for inspiration and a second set of body plots 1102b–1108b similarly corresponding to a particular chest region for expiration. Within each body plot 1102–1108 is a set of markers 1110 each corresponding to a particular microphone site. Each marker 1110, moreover, is preferably color-coded to reflect the intensity of the computed RMS level for that site. A color coded scale 1112 of RMS levels is also provided, where blue corresponds to relatively low RMS intensity levels and red corresponds to relatively high RMS intensity levels.

Review of graphical display 1100 by the attending physician may provide substantial information. For example, the presence of fluid in a patient's pleural space (i.e., the area between the chest wall and the lungs and against which the lungs slide) has been found to cause a marked decrease in sound intensity over the affected area. The identification of this condition may be rapidly and accurately determined by means of a review of display 1100. In particular, areas with relatively low RMS values (i.e., low sound intensity) are indicated in display 1100 by blue designations 1110. Accordingly, the presence of fluid in the pleural space often manifests as blue designations 1110, especially where adjacent red designations (i.e., areas of high sound intensity) are also present.

It should be understood that, for a given signal trace, separate RMS values may be calculated for those portions of the signal trace representing adventitious sounds and those portions which do not correspond to adventitious sounds.

Automatic Localization of Adventitious Sounds

In the preferred embodiment, the system 100 (FIG. 1) further includes an automatic localization program 205 (FIG. 2), which reviews the results obtained from the adventitious sound detection program 203 and determines the physical location, i.e., the coordinates, in three-dimensions (3-D) of the point of origin of one or more adventitious sounds that have been identified. As described herein, program 205 may also be used to automatically compute the point of origin of normal body sounds.

Figure 14A:
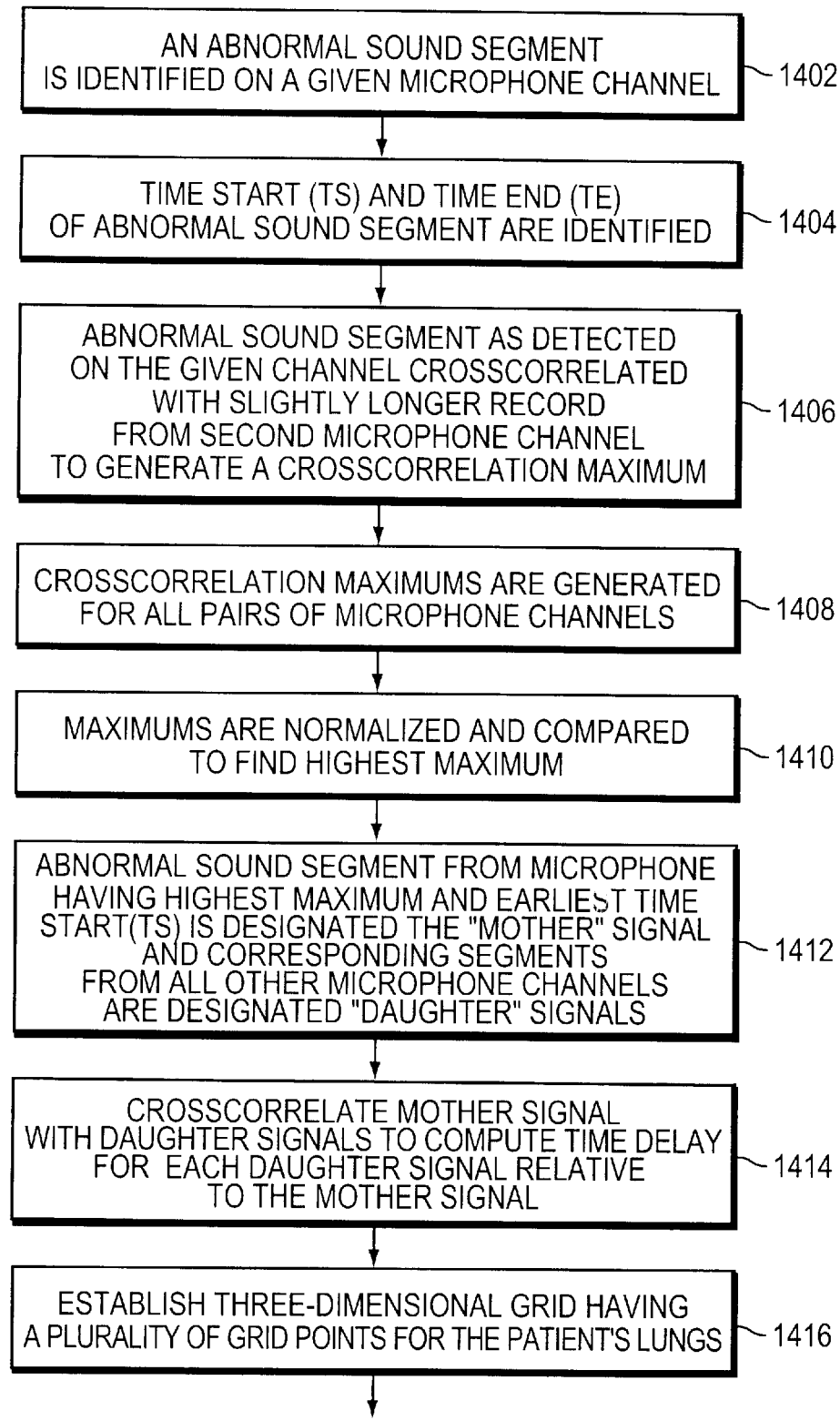
FIGS. 14A–14B is a flow diagram of a preferred localization method in accordance with an aspect of the present invention.
Figure 14B:
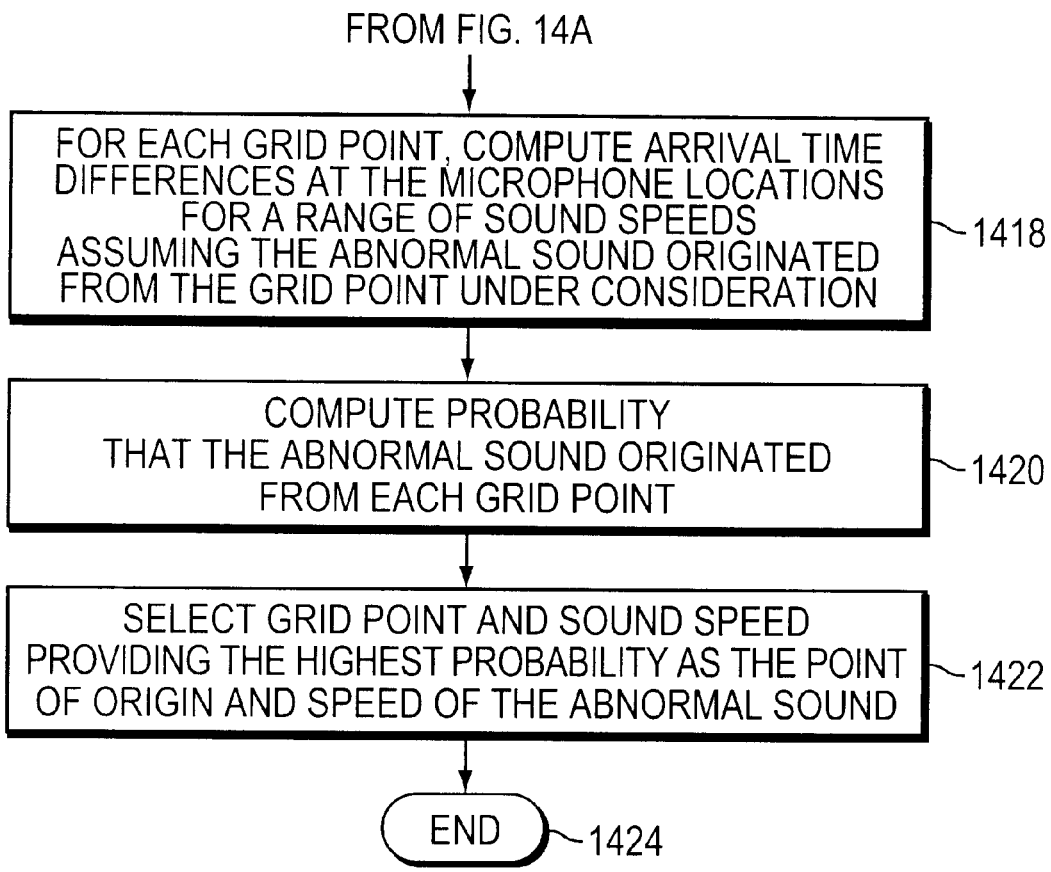

FIGS. 14A–14B is a flow diagram of the preferred localization method of the present invention. First, an abnormal sound segment, such as a crackle, is identified on a given channel, as indicated by block 1402. Next, the start time (ts) and end time (te) of the abnormal sound segment are identified, as indicated by block 1404. The abnormal sound segment, from ts to te, is then cross-correlated with a slightly longer record from a second microphone channel, as indicated at block 1406, namely, from ts minus several milliseconds (ms) to te plus approximately 40 ms. The resulting cross-correlation maximum is preferably retained, as also indicated at block 1406. This procedure is preferably repeated for the signals from all sites, thereby producing cross-correlation maximums for all pairs of microphones, as indicated at block 1408. All cross-correlation maximums are then normalized by the amplitude of the abnormal sound segment from the first channel evaluated, and compared to locate the highest cross-correlation maximum, as indicated at block 1410. The abnormal sound segment from the microphone channel having the highest maximum correlation and the earliest start time is designated to be the "mother" signal, while all others are designated to be "daughter" signals, as indicated at block 1412.

Figure 15:
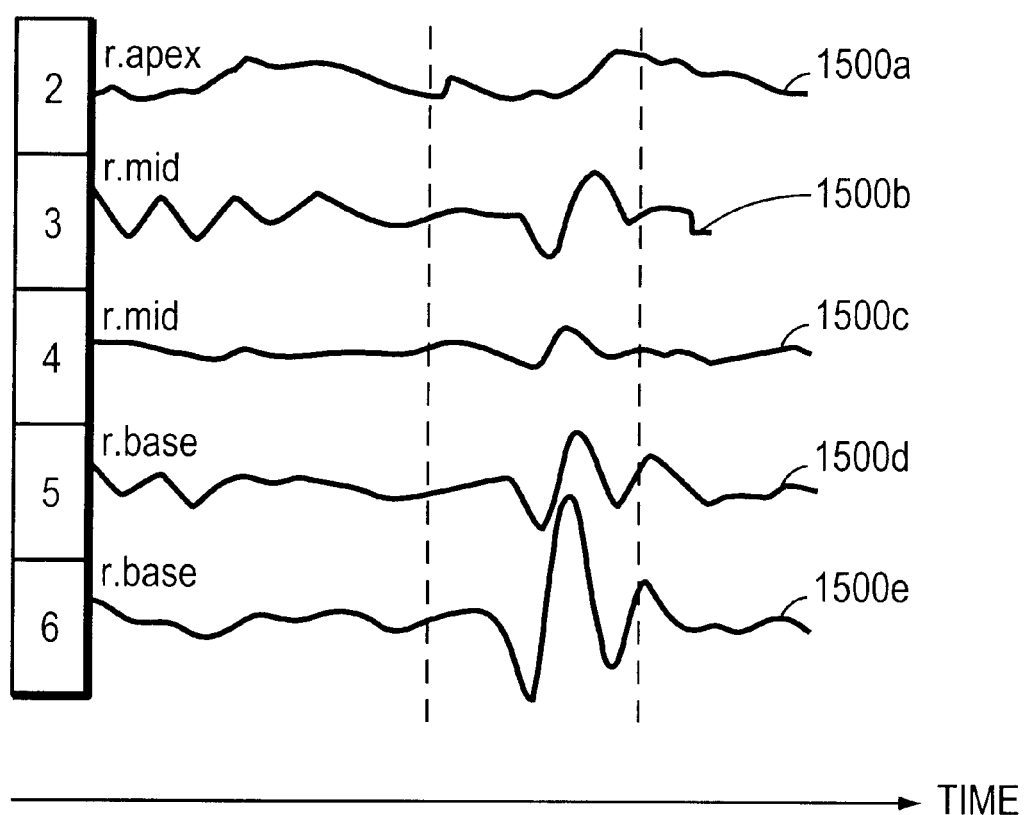
FIG. 15 is a highly schematic illustration of an abnormal sound segment as detected at a plurality of microphone channels in amplitude versus time format.

FIG. 15 is a highly schematic illustration of a plurality of signals or traces 1500a–e in amplitude versus time format showing a "mother" signal and a plurality of "daughter" signals. More specifically, signal 1500e, which has the highest energy in the relevant frequency range and the earliest arrival time, will be designated as the "mother" signal, while the remaining signals 1500a–d will each be designated as "daughter" signals.

Next, the mother signal and all daughters signals are cross-correlated to compute the time delay for each daughter signal relative to the mother signal, as indicated at block 1414. A three-dimensional grid having a plurality of points or cells is then established, as indicated at block 1416. The grid logically encompasses all or any part of the patient's thorax, e.g., the lungs. That is, the patient's thorax is represented by the grid. The grid is preferably on the order of 40 centimeters (cm) wide (x), 20 cm high (y) and 20 cm deep (z). Within the grid are a plurality of grid points with a resolution of 1 cm in all three dimensions. The program 205 considers each grid point and determines the probability that the abnormal sound being evaluated originated from that grid point. Specifically, for every grid point, program 205 computes the arrival time differences at each microphone location assuming the sound originated from the grid point currently being evaluated, as indicated at block 1418 (FIG. 14B). The location of the sound source (i.e., the grid point under evaluation) and the location of the microphones are all known. In addition, program 205 utilizes an assumed sound speed. Rather than using a single assumed sound speed, however, the program 205 preferably evaluates a range of sound speeds for each grid point. In particular, arrival times are computed with the sound speed moved in increments of 2 centimeters/millisecond (cm/ms) between the range of 2 to 12 cm/ms.

A probability that the abnormal sound originated from the grid point being evaluated is then computed, as indicated at block 1420. The probability of the selected grid point and sound speed may be a weighted sum of the difference between the computed arrival time difference and the measured arrival time difference for all microphone pairs. The weight may be a corresponding correlation coefficient. The grid point and sound speed having the highest probability is then selected as the origin of the respective sound, as indicated at block 1422. Processing by the localization program 205 is then complete, as indicated by end block 1424. The localization algorithm is preferably run in real-time, i.e., as the body sounds are being received by the system.

It should be understood that other methods of sound localization may be utilized.

Three-Dimensional Displays

Figure 16:
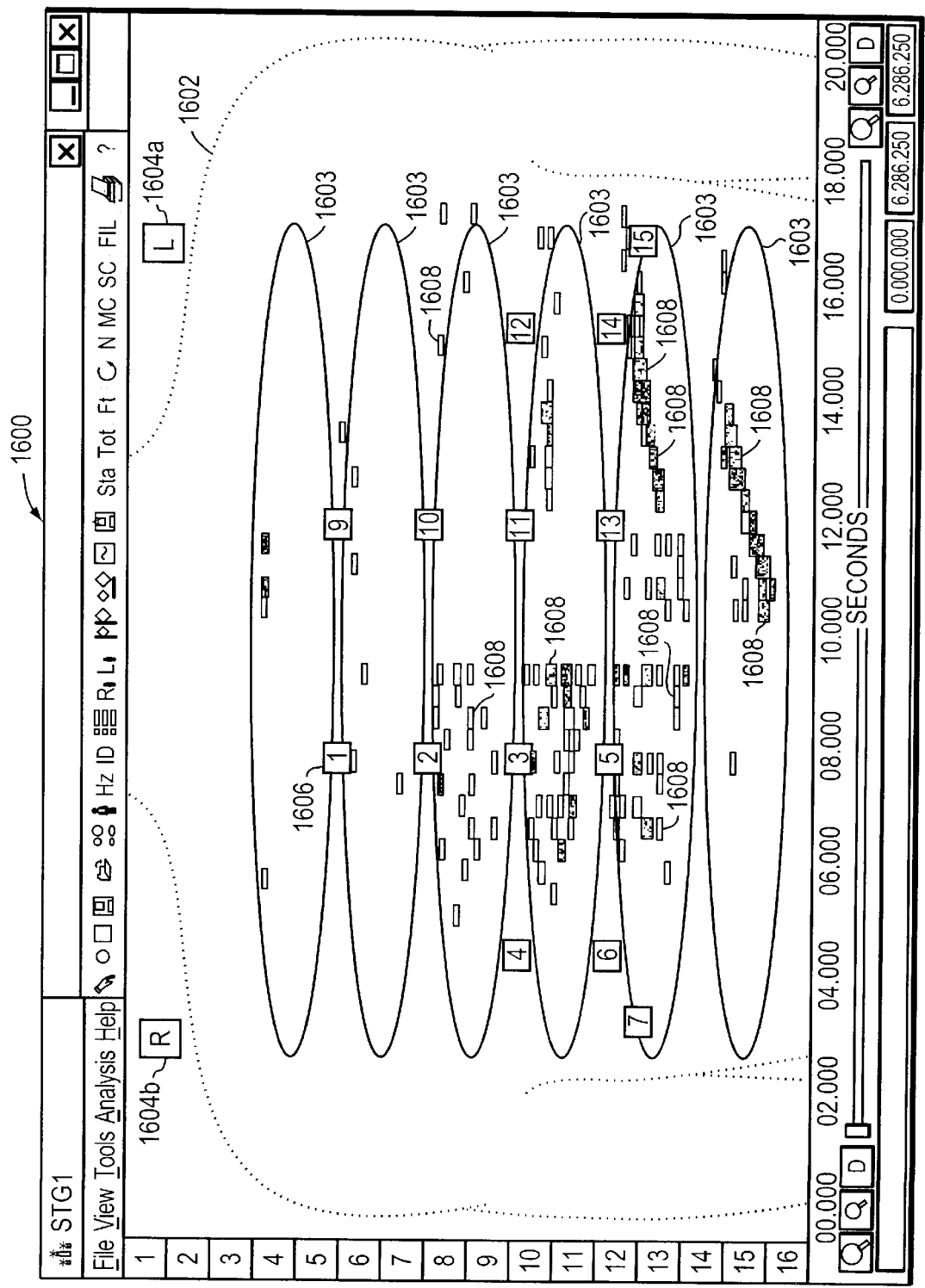
FIGS. 16 and 17 are representative three-dimensional displays of adventitious sounds in accordance with an aspect of the present invention.

Once the origin of the abnormal sound has been determined, that information can be provided to the attending physician in a number of ways. For example, it can be displayed on the graphical user interface 126. FIG. 16 is a highly schematic exemplary display 1600 of localization information which may be presented on the graphical user interface 126 and reviewed by the attending physician. Display 1600 is a three-dimensional representation of at least a portion of the patient. It may include an outline or profile 1602 of a human body or a portion thereof, such as a chest area, and a plurality of parallel, horizontal image planes 1603. In addition, left (L) 1604a and right (R) 1604b markings may be provided to indicate whether the profile 1602 is of the patient's front or back. The profile 1602 and image planes provide a point of reference for the location of detected abnormal sounds that are also displayed. A plurality of numeric markings 1606, e.g., 1–7 and 9–15, may be provided that correspond to the microphone sites. Microphone number "8" which is located at the patient's heart is not included in the display 1600.

As the previously recorded data of a patient's breathing, i.e., inspiration and expiration, is played back, indicators or markings 1608 appear at the point of origin of adventitious sounds. These markings may be generally rectangular or they may take other shapes. Preferably, the markings 1608 appear at the time the respective adventitious sound was detected and disappear shortly thereafter. For example, the color of the markings 1608, as described below, may be faded by approximately 30% after 100 milliseconds (ms) of its first appearance. After 200 ms, the color may be faded by another 30% and so on until about 700 ms after the marking's first appearance at which point it is faded to about 5% of its original color. Alternatively, the color may fluctuate with the intensity of the abnormal sound, and completely disappear when the abnormal sound is no longer being detected.

The markings 1608 of FIG. 16 correspond to abnormal sounds, such as crackles and wheezes, identified by the adventitious sound detection program 203 and localized by the localization program 205. Color codings may be used to distinguish between crackles and wheezes. Crackles, for example, may be illustrated by markings 1608 that range from gray to black depending on their intensity, i.e., the number of detected crackles at that location or space. Black being high intensity while gray represents low intensity. Wheezes, on the other hand, may be represented by markings that range in color from yellow to dark red depending on the intensity with yellow being low intensity and red being high intensity. Large areas, such as the patient's lower left lung area, having many concentrated crackles may be indicative of pneumonia On the other hand, if the crackles appear distributed widely across the lungs, especially toward the base, it may be indicative of congestive heart failure.

This real-time, video style display can be generated from previously recorded or stored data or it can be generated in real-time as the patient breathes. FIG. 16 thus corresponds to a snap-shot of this video-style playback.

Figure 17:
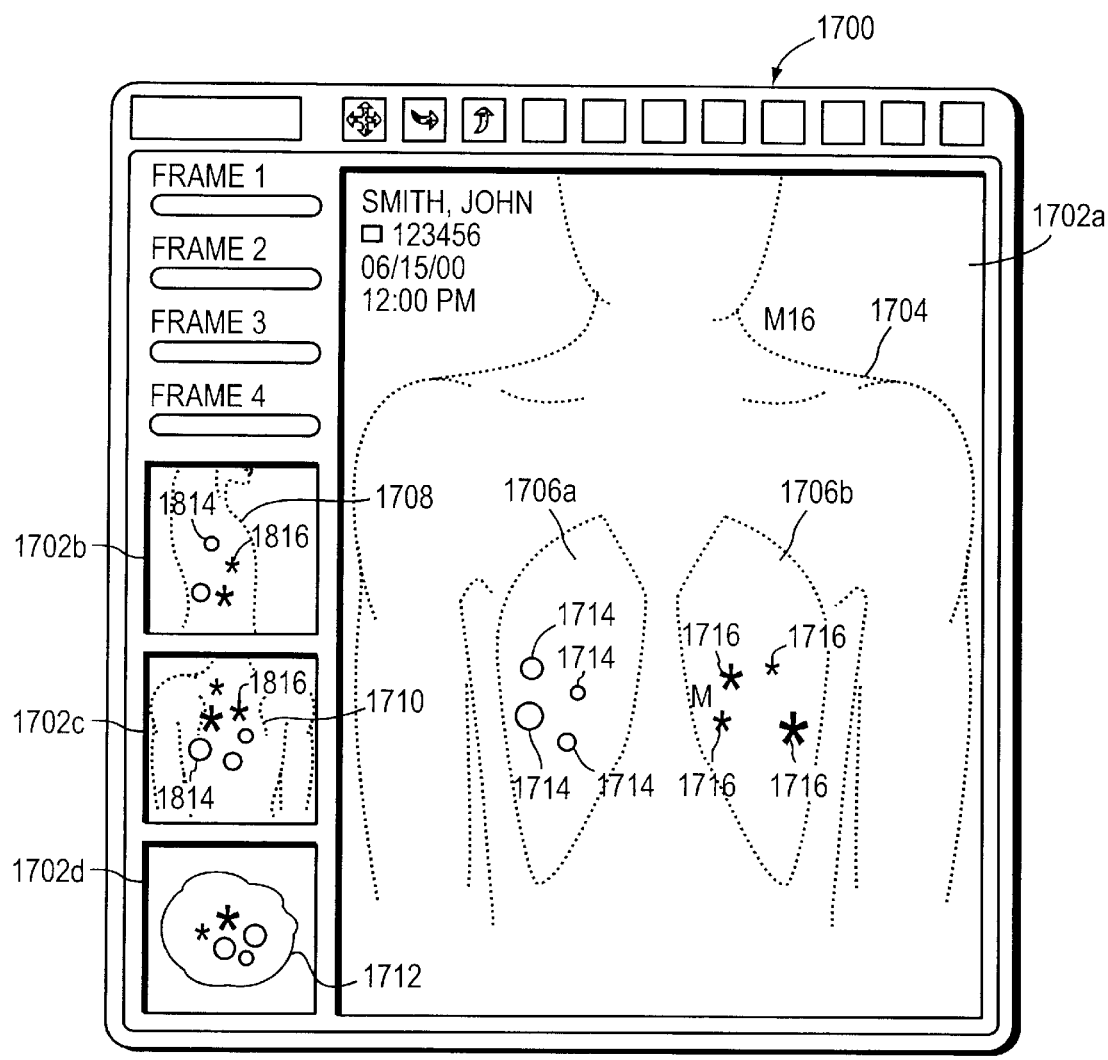

FIG. 17 is another exemplary three-dimensional representation 1700 illustrating localization information as computed by the system 100 of the present invention. As shown, the display 1700 includes four areas 1702a–d. A first area 1702a contains a front view of the patient. The front view includes an outline or profile 1704 of the patient and representative lung images 1706a–b. Second area 1702b contains a back view of the patient including an outline or profile 1708. Third area 1702c contains a side view, e.g., left side, of the patient including an outline 1710. Fourth area 1702d contains a sectional view of the patient at a selected elevation. It may also include a corresponding outline or profile 1712.

Glyphs are preferably displayed within the profile displayed in each area 1702a–d to illustrate and represent the detection of abnormal sounds. In the illustrative embodiment, spheres 1714 are used to represent wheezes, while stars 1716 are used to represent crackles. The size of each glyph can be adjusted to reflect the number of occurrences, e.g., density, of the respective adventitious sound at that location, i.e., the larger the glyph the more adventitious sounds were detected.

It should be understood that a user may manipulate cutting planes within the first area 1702a to generate the displays shown in the second to fourth areas 1702b–d. Patient information as well as a legend may also be displayed. The display 1700 can be configured to show information in a static format, i.e., all abnormal sounds detected in the relevant time period. Alternatively, it may be configured to show information in a dynamic, real-time format, i.e., with the glyphs appearing upon detection of the respective abnormal sound and disappearing at their conclusion. Again, a color scale may be implemented to represent sound intensity with darker colors representing higher intensities.

Those skilled in the art will recognize that other displays of abnormal sounds and their localization can be created.

Automatic Localization of Normal Sounds

The automatic localization program 205 may also be used to determine the origin, i.e., the physical coordinates, of normal body sounds. There are benefits to localization of normal sounds. For example, during expiration sounds are mostly produced in the large airways. Localization of these sounds corresponds to the location of the large airways of a patient. Thus, adventitious sounds can be localized relative to these large airways.

Additionally, since sounds during inspiration are mostly produced peripherally, the location of these normal inspiratory sounds can provide information on which areas of the lung are the best and worst ventilated.

Probable-Diagnosis Prediction Program

In the preferred embodiment, the system 100 (FIG. 1) further includes a probable-diagnosis prediction program 204 (FIG. 2), which reviews the results obtained from the adventitious-sound detection program 203 and preferably provides a proposed diagnosis based upon those results. This program 204 may be based on a neural network module, such as the neural network programming tools from The Mathworks, Inc. or other statistical classification methods. The probable-diagnosis prediction program 204 preferably interacts with a training database 207 to derive the proposed diagnosis. In particular, the training database 207 preferably contains a set of adventitious lung sound data from patients previously diagnosed with various pulmonary diseases, such as COPD, asthma, IPF, etc. More specifically, the training database 207 includes typical data corresponding to the ratio of inspiration to expiration, the numbers and locations of coarse, medium, and fine crackles, wheezes, and rhonchi, and RMS values commonly associated with these diseases. The probable-diagnosis prediction program 204 compares the results obtained by the adventitious-sound detection program 203 for the given patient with the information in the training database and provides a proposed diagnosis, which represents the particular disease which most closely matches the results obtained for the given patient.

It should be understood that the probable-diagnosis prediction program 204 may alternatively utilize multiple logistic regression models to arrive at a proposed diagnosis. A suitable multiple logistic model approach is described in P. Bettencourt, E. Del Bono, D. Spiegelman, E. Hertzmark and R. Murphy, Jr. *Clinical Utility of Chest Auscultation in Common Pulmonary Diseases* Vol. 150, No. 5 American Journal of Respiratory and Critical Care Medicine (November 1994), which is hereby incorporated by reference in its entirety.

Input Sounds

Sounds may also be input to the patient in order to generate useful information that can be detected by the system 100 of the present invention. The sounds may be patient generated or they may be externally generated. The externally generated sounds can be input to the patient by a mouthpiece 123 (FIG. 1) having one end connected to the speaker 121 and the other end inserted into a patient's mouth. The mouthpiece 123 may simply be a hollow cylinder, such as a disposable paper or plastic tube. The sound enters the patients airways, travels through his or her lung tissue and is detected by the microphones 102. The properties of the patient's lung and other tissue through which the sound travels before being detected by the microphones 102 affect the sound's characteristics. Depending on when and how the input sound is detected can provide information regarding these properties.

One parameter that can be measured, for example, is time delay. Time delay, which refers to the amount of time it takes for the input sound to be detected at the microphones 102, is a function of the speed of sound in the lung tissue. Speed of sound, moreover, is a function of lung characteristics such as the presence or absence of fluid, vapor, the morphology of lung tissue, etc. Also, the speed of sound is three to fifteen times faster in air than lung tissue. A patient with emphysema, moreover, typically has areas of his or her lung tissue missing, i.e., destroyed air sacs. Therefore, a physician would often detect unusual increase in sound speed, i.e., less time delay, in the affected areas of such a patient, as the sound would be travelling through some pockets of air rather than lung tissue.

Figure 18:
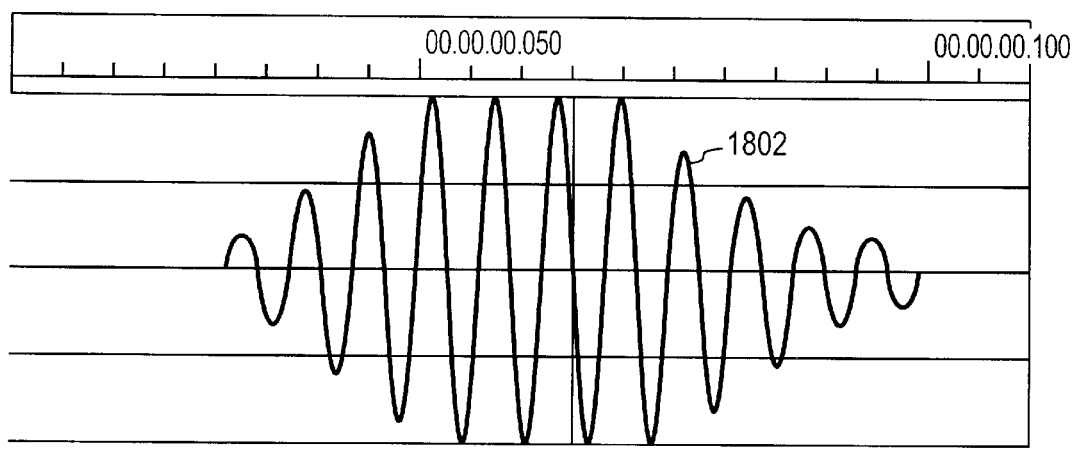
FIG. 18 is an exemplary representation of an input sound signal in accordance with an aspect of the present invention.

The input sounds may be continuous, such as white noise, or discontinuous. FIG. 18 illustrates an example of a discontinuous input sound signal 1802 in amplitude versus time format. The input sound signal 1802 is preferably a hybrid of many frequencies. In the illustrative embodiment, it starts at 150 Hz and ends at 170 Hz. More specifically, the frequency of the input sound changes by about 10% every cycle. This varying frequency signal aids in accurately determining time delay, especially when the time delay is about one period.

It should be understood that an externally generated input sound may be input to the patient at a location other than the patient's mouth. For example, the end of the mouthpiece may be placed at a location on the patient's neck, chest, back or side, among other places.

Acoustic Resonance

Figure 19:
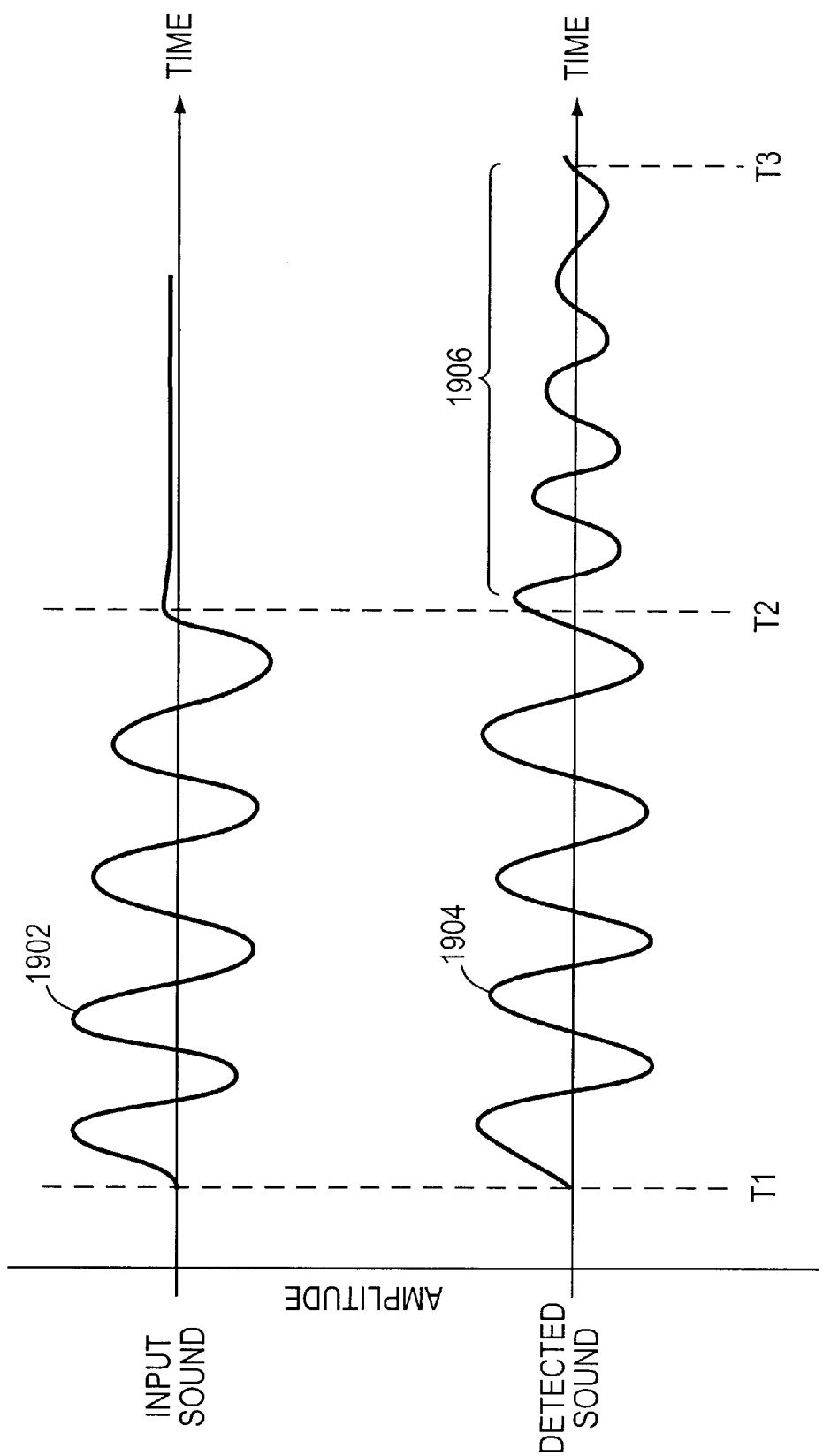
FIG. 19 is an exemplary representation of an input sound signal and a detected sound signal in amplitude versus time format.

Application of an input sound may also result in the generation of acoustic resonance. Acoustic resonance is the continuation of sound from within the body after the input sound has terminated. FIG. 19 is an amplitude versus time plot of two signals illustrating the phenomenon of acoustic resonance. FIG. 19 includes an input sound plot 1902 and a detected sound plot 1904 that is picked up by a respective microphone 102 (FIG. 1). It should be understood that the input sound plot 1902 may correspond to the input sound as detected by the microphone 102 located at the patient's trachea or it may be a plot of the actual input sound. The input sound plot 1902 begins at a selected start time T1 and is terminated at a selected end time T2. The time duration of the input sound, i.e., T2 minus T1, is preferably on the order of 0.5 seconds. As shown, the detected sound plot 1904 begins shortly after T1. However, in some circumstances, the detected sound plot 1904 continues well past, e.g., for several more seconds or more, the time T2 at which the input sound is terminated. This extension or continuation of the detected sound, which is referred to herein as acoustic resonance, is designated generally by reference number 1906. As indicated, the acoustic resonance 1906 extends from approximately time T2 to an end time T3.

The length of time of the acoustic resonance signal and its frequency or frequencies can provide information regarding the condition of the patient's lungs. For example, in normal persons, the resonance may be commonly observed at all sites. However, in patient's suffering from emphysema, the observed resonance is significantly reduced.

Sound Sensor Cassette

Figure 21:
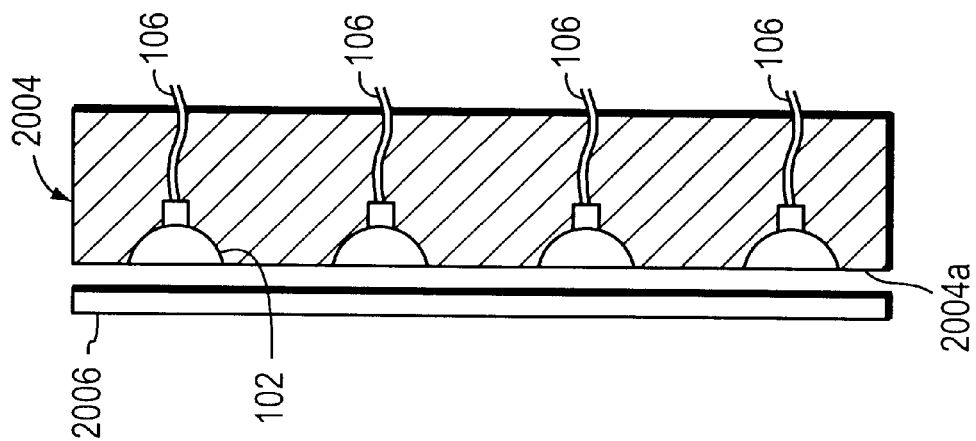
FIGS. 20–22 are a highly schematic illustrations of a microphone cassette in accordance with another aspect of the present invention.
Figure 20:
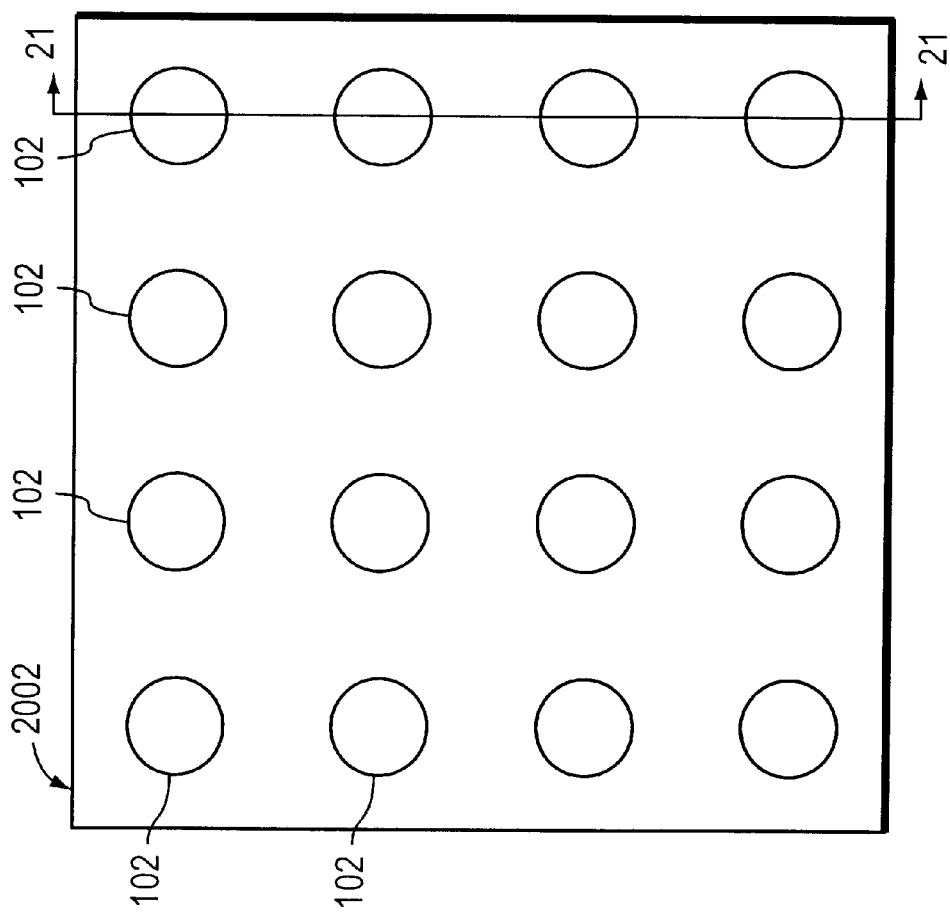

In a further aspect of the present invention, a plurality of microphones may be embedded within a single structure to form a cassette. FIGS. 20 and 21 are highly schematic illustrations of a cassette 2002 in plan and cross-section views. The cassette 2002 houses a plurality of microphones 102. In the illustrative embodiment the microphones are arranged in a 4×4 array that is generally square or rectangular. The cassette 2002 further includes a core 2004 (FIG. 21), preferably made from foam, for supporting the microphones 102. Specifically, recesses are formed in the foam core 2004 to receive the microphones 102 such that the microphones 102 are flush with an upper surface 2004a of the core 2004. Leads 106 from the microphones 102 preferably extend through the core 2004.

In the preferred embodiment, the cassette 2002 further includes a disposable interface 2006 that covers at least the entire upper surface 2004a. The interface is preferably formed from a hospital grade "clean-wrap". The interface 2006 may be attached to the core 2004 of the cassette in a variety of ways, such as by tape, clips, fasteners, etc. In an alternative embodiment, the interface 2006 may surround and cover the entire core 2004.

The cassette 2002 may be positioned on a hospital bed (not shown) between the mattress and a patient. The cassette 2002 may also be reused by simply replacing the interface 2006. By incorporating the microphones 102 within the cassette 2002, the microphones 102 can be quickly and easily positioned to a location of interest to the attending physician. Indeed, the cassette 2002 in cooperation with the system 100 of the present invention can be used to locate intestinal obstructions. Such obstructions typically generate substantial noises. Here, the cassette 2002 can be easily moved to different locations on the patient's abdomen. By using the cassette 2002 in cooperation with the localization program 205 described above, the location of a patient's intestinal obstruction can be determined non-invasively. The cassette 2002 can also be utilized to monitor heart murmurs. In this cases, the cassette 2002 is preferably placed on the patient's chest preferably near his or her heart. Again, cooperation of the microphones 102 of the cassette with is the localization program 205 allow an attending physical to pin point the point of origin of heart murmurs.

Figure 22:
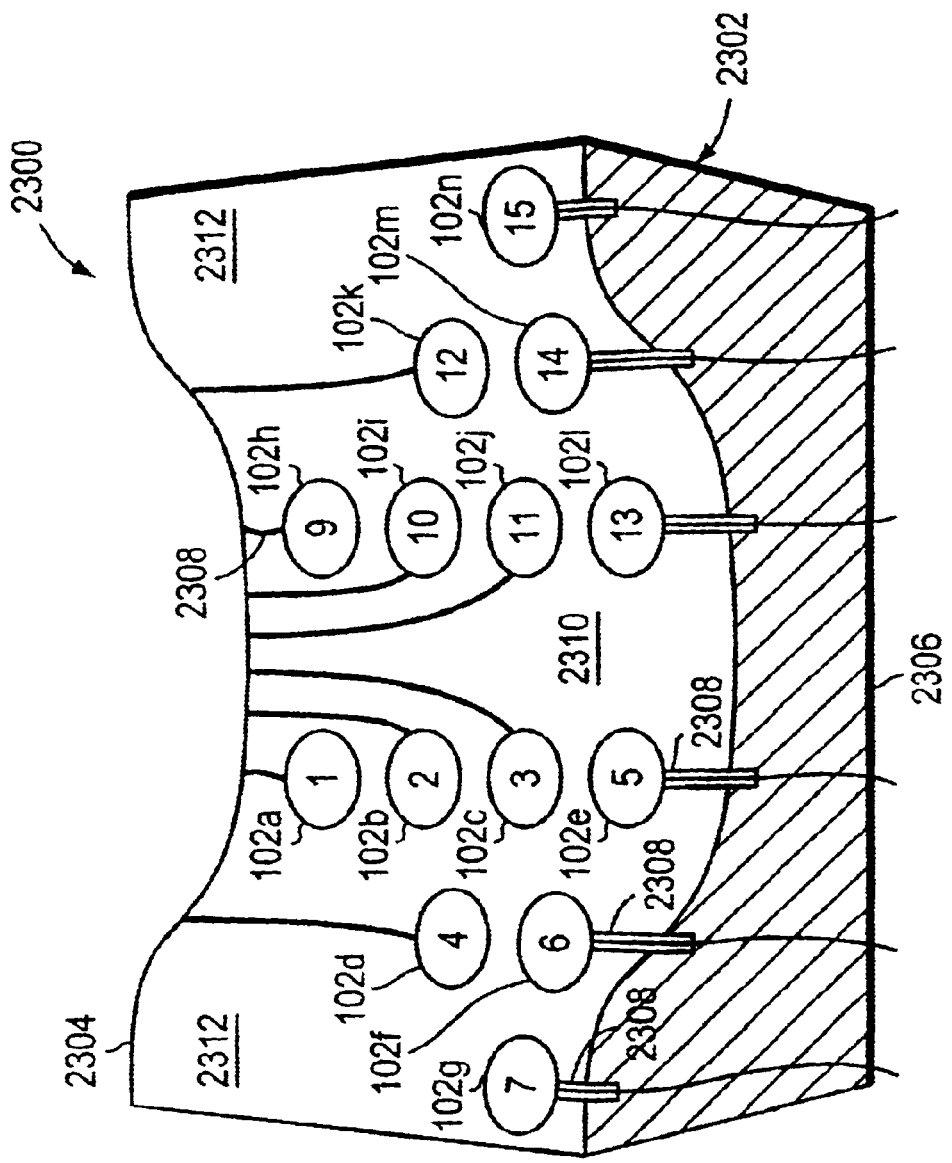

FIG. 22 is a perspective view of a preferred embodiment of a cassette 2300 having a core structure 2302 that is preferably formed from a foam. Core structure 2302 defines a contoured upper surface 2304 and a substantially flat lower surface 2306. Disposed with the core structure 2302 are a plurality of microphones 102a-. As with the cassette 2002 of FIGS. 20 and 21, recesses are formed in the core 2302 to receive the microphones 102 such that the upper portions of the microphones 102 are flush with the contoured upper surface 2304. Narrow slots 2308 are preferably formed, e.g., cut, in the core to receive the leads from the microphones 102. As shown, upper surface 2304 is contoured such that a central area 2310 is recessed relative to two side areas 2312 of the core 2302.

As with cassette 2002, cassette 2300 is preferably positioned on a hospital bed (not shown) between the mattress and a patient. Furthermore, the patient lies in either a horizontal or slightly inclined position on the cassette, such that the patient's spine is substantially aligned along the central area 2310, and the side areas 2312 are proximate to the patient's sides. A disposable cover (not shown) may be placed over the cassette 2300 or at least upper surface 2304.

Distinguishing Between IPF and CHF Based on Crackle Analysis

Crackles often occur in patients suffering from both interstitial pulmonary fibrosis (IPF) and from congestive heart failure (CHF). As the crackles can sound very similar in both cases, it can be difficult to distinguish between the two conditions. In another aspect of the present invention, a system and method have been developed for differentiating between the crackles produced by an IPF patient from the crackles produced by a CHF patient.

Generally speaking, crackles produced by a patient with CHF are typically transmitted over a larger area of the lung(s), e.g., an area that is roughly 4 inches by 4 inches, than the crackles of a patient with IPF which are transmitted over a much smaller area, e.g., an area that is roughly 2 inches by 2 inches.

In the illustrative embodiment of this aspect of the invention, the adventitious sound detection program 203 is further configured to compute a novel value, referred to herein as the transmission coefficient. First, as described above, for each crackle detected during one or more inspiration phases of a patient's breathing, the mother crackle and corresponding daughter crackles are identified. Next, the signal corresponding to each identified mother crackle is crosscorrelated with the signals corresponding to the respective daughter signals, as described above, thereby producing a crosscorrelation function that has a peak value. Additionally, the signal corresponding to each mother crackle is autocorrelated to produce an autocorrelation function having a peak. For each set of mother crackle and corresponding daughter crackles, program 203 calculates the ratio of the peak of the crosscorrelation function to the peak of the mother crackle autocorrelation function. The calculated ratios, which characterize the degree of sound transmission from the sound source to the chest, are then averaged to generate the transmission coefficient. The transmission coefficient has a value of 0% in the absence of any transmission of the adventitious sound beyond the one location or channel at which it is detected and 100% when there is equal transmission to all locations or channels.

In the illustrated embodiment, the adventitious sound detection program 203 is further configured to display a calculated transmission coefficient, which can be used by an attending physician in arriving at a diagnosis.

Furthermore, as indicated above, each crackle detected by program 203 has a corresponding frequency. In the preferred embodiment, program associates the frequency of the mother crackle with the computed transmission coefficient. Program 203 also computes an average crackle frequency by averaging the frequency between all crackle families, which is then associated with the average transmission coefficient.

Experimental tests have shown that for a given average frequency, the transmission coefficient for a CHF patient is noticeably and statistically higher than the transmission coefficient for an IPF patient. A transmission coefficient higher than 0.03×F+6, where F is the frequency in Hertz (Hz) associated with the transmission coefficient indicates a high likelihood of CHF, while a transmission coefficient lower than 0.03×F+6 indicates a high likelihood of IPF.

Accordingly, in a further embodiment, program 203 also displays a two-dimensional plot of transmission coefficient (preferably on the vertical axis) versus frequency on the horizontal axis. The plot, moreover, is preferably separated into upper and lower halves by a line corresponding to the following equation $$\text{transmission coefficient} = 0.03F + 6$$

The position of a given calculated average transmission coefficient onto this plot by program 203 assists the attending physician in differentiating a CHF diagnosis with an IPF diagnosis. In particular, as mentioned above, if the position of the calculated average transmission coefficient falls above this line suggests CHF, while a position below this line suggests IPF.

The foregoing description has been directed to specific embodiments of this invention. It will be apparent, however, that other variations and modifications may be made to the described embodiments with the attainment of some or all of their advantages. Accordingly, this description should be taken only by way of example and not by way of limitation. It is the object of the appended claims to cover all such variations and modifications as come within the true spirit and scope of the invention.

What is claimed is:

1. A diagnostic system for use with a patient, the diagnostic system comprising:

a plurality of transducers for placement at various sites around the patient, the transducers configured to generate signals that are responsive to sounds from within the patient;

a sound localizer configured to receive the signals generated by the plurality of transducers for a given sound and to calculate a set of three dimensional coordinates corresponding to an origin of the given sound; and a display screen operatively coupled to the sound localizer, wherein the sound localizer generates a three-dimensional representation of the patient that includes at least one partial profile and one or more markings for the given sound, the one or more markings appearing on the three-dimensional representation in relation to the calculated coordinates.

2. The diagnostic system of claim 1 wherein the three-dimensional representation includes one or more image planes, each image plane corresponding to a virtual cross-section of the patient.

3. The diagnostic system of claim 2 wherein the image planes are parallel to each other and aligned horizontally relative to an upright position of the patient.

4. The diagnostic system of claim 2 wherein the markings appear on the image planes.

5. The diagnostic system of claim 1 further comprising an adventitious sound detector configured to receive and analyze the signals generated by the plurality of transducers so as to identify one of an adventitious and a normal sound, and further wherein the given sound for which three-dimensional coordinates are calculated corresponds to an adventitious or a normal sound identified by the adventitious sound detector.

6. The diagnostic system of claim 5 wherein the detected adventitious sounds include at least one of crackles and wheezes.

7. The diagnostic system of claim 6 wherein the display is continuous running display while the patient breathes, and the markings appear on the three-dimensional representation at the point in times at which the respective adventitious sounds are detected.

8. The diagnostic system of claim 5 wherein the sound localizer utilizes cross-correlation techniques as applied to a plurality of signals that correspond to the same adventitious or normal sound event to calculate the three-dimensional coordinates of the adventitious or normal sound event.

9. The diagnostic system of claim 8 wherein the sound localizer computes a probability that the adventitious or normal sound event under analysis originated from a plurality of locations within the patient, and selects the location having the highest probability as the three-dimensional coordinates for the respective adventitious or normal sound event under analysis.

10. The diagnostic system of claim 9 wherein a probability is computed for each location over a range of assumed sound speeds, and the location and sound speed presenting the highest probability are selected as the three-dimensional coordinates and sound speed for the respective adventitious or normal sound event under analysis.

11. The diagnostic system of claim 5 wherein the sound localizer and the adventitious sound detector are application programs running on a computer system.

* * * * *